(12) United States Patent
Hedrick et al.

(10) Patent No.: US 7,205,381 B2
(45) Date of Patent: Apr. 17, 2007

(54) MAMMALIAN CYTOKINES; RELATED REAGENTS AND METHODS

(75) Inventors: Joseph A. Hedrick, Plainsboro, NJ (US); Theodore R. Sana, East Palo Alto, CA (US); J. Fernando Bazan, Menlo Park, CA (US); Robert A. Kastelein, Redwood City, CA (US)

(73) Assignee: Schering Corporation, Kenilworth, NJ (US)

( * ) Notice: Subject to any disclaimer, the term of this patent is extended or adjusted under 35 U.S.C. 154(b) by 622 days.

(21) Appl. No.: 09/770,528

(22) Filed: Jan. 25, 2001

(65) Prior Publication Data

US 2002/0164332 A1 Nov. 7, 2002

Related U.S. Application Data

(60) Division of application No. 09/130,972, filed on Aug. 7, 1998, now abandoned, which is a continuation of application No. 09/097,976, filed on Jun. 16, 1998, now abandoned, which is a continuation of application No. 09/062,866, filed on Apr. 20, 1998, now abandoned.

(60) Provisional application No. 60/055,111, filed on Aug. 6, 1997, provisional application No. 60/044,165, filed on Apr. 21, 1997.

(51) Int. Cl.
   *C07K 16/00* (2006.01)
(52) U.S. Cl. ............... 530/300; 530/350; 530/387.1; 530/387.9
(58) Field of Classification Search ............. 424/130.1, 424/133.1, 139.1, 141.1, 145.1, 158.1; 530/387.1, 530/387.3, 387.9, 388.1, 388.23, 388.24, 530/589.1, 389.2, 391.3, 350.1, 358.1, 358.15, 530/389.1, 391.1
See application file for complete search history.

(56) References Cited

U.S. PATENT DOCUMENTS

| 5,194,596 | A | * | 3/1993 | Tischer et al. |
| 5,350,836 | A | * | 9/1994 | Kopchick et al. |
| 5,945,310 | A | | 8/1999 | Young et al. |
| 2002/0187122 | A1 | | 12/2002 | Sims |

FOREIGN PATENT DOCUMENTS

EP   0 541 920 A1   5/1993

OTHER PUBLICATIONS

Benjamin et al., 1998, Development 125:1591-1598.*
Vukicevic et al., 1996, PNAS USA 93:9021-9026.*
Massague, 1987, Cell 49:437-438.*
Pilbeam et al., 1993, Bone 14:717-720.*
Skolnck et al., 2000, Trends in Biotech 18:34-39.*
Bork, 2000, Genome Research 10:398-400.*
Doerks et al., 1998, Trends in Genetics 14:248-250.*
Smith et al., 1997, Nature Biotechnology 15:1222-1223.*
Murdoch et al., 2000, Blood 95:3032-3043.*
Ji et al., 1998, J.Biol. Chem. 273:17299-17302.*
P.E. Auron, et al., *GenPept*, Accession No. 124303, Jul. 15, 1998. Definition: Interleukin-1 Beta Precursor (IL-1Beta) (Catabolin).
J. Fernando Bazan, et al., *Nature*, 379:591, Feb. 15, 1996. "A newly defined interleukin-1?".
Marcia P. Belvin, et al., *Annu. Rev. Cell Dev. Biol.*, 12:393-416, 1996. "A Conserved Signaling Pathway: The *Drosophilia* Toll-Dorsal Pathway".
M.J. Carrier, *GenBank*, Accession No. X64532, Jun. 25, 1997. Definition: "H.sapiens gene for interleukin-1 receptor antagonist".
D.B. Carter, et al., *GenPept*, Accession No. 124312, Jul. 15, 1998. Defintion: Interleukin-1 Receptor Antagonist Protein Precursor (IL-1RA) (ICIL-1RA) (IRAP)
Fabio Cominelli, et al., *Journal of Biological Chemistry*, 296(9):6962-6971, Mar. 4, 1994. "Rabbit Interleukin-1 Receptor Antagonist".
F. Cominelli, et al., *GenBank*, Accession No. S68977, Sep. 22, 1994. Definition: "sIL-1ra=interleukin-1 receptor antagonist secreted form [rabbits, colon tissue, mRNA, 574 nt.]".
Charles A. Dinarello, *Blood*, 77(8):1627-1652, Apr. 15, 1991. "Interleukin-1 and Interleukin-1 Antagonism".
Charles A. Dinarello, *The FASEB Journal*, 8:1314-1325, Dec. 1994. "The interleukin-1 family: 10 years of discovery".
W.H. Gilmore, et al., *GenBank*, Accession No. Z70047, Mar 11, 1996. Definition: "C.familiaris mRNA for interleukin-1 beta".
F. Goto, et al., *GenBank*, Accession No. D21832, Apr. 21, 1994. Definition: "Rabbit mRNA for interleukin-1 receptor antagonist, complete cds."
Angela M. Gronenborn, et al., *Protein Engineering*, 4(3):263-269, 1991. "Modeling the three-dimensional structure of the monocyte chemo-attractant and activating protein MCAF/MCP-1 on the basis of the solution structure of interleukin-8".
H. Hamada and R.C. Mulligan, et al., *GenBank*, Accession No. M57526, Jan. 30, 1992. Definition: "Rabbit interleukin-1 receptor antagonist (IL1RA) mRNA, complete cds."

(Continued)

*Primary Examiner*—Elizabeth Kemmerer
(74) *Attorney, Agent, or Firm*—Laurie L. Hill; Edwin P. Ching

(57) ABSTRACT

Nucleic acids encoding mammalian, e.g., rodent, IL-1δ, IL-1ε, purified IL-1δ and IL-1ε proteins and fragments thereof. Antibodies, both polyclonal and monoclonal, are also provided. Methods of using the compositions for both diagnostic and therapeutic utilities are provided.

10 Claims, 3 Drawing Sheets

OTHER PUBLICATIONS

C.H. Hannon, et al., *GenBank*, Accession No. I09591, Nov. 14, 1994. Definition: "Sequence 1 from Patent WO 8911540".

C.H. Hannon, et al., *GenBank*, Accession No. I09592, Nov. 14, 1994. Definition: "Sequence 3 from Patent WO 8911540".

J.K. Jenkins, et al., *GenBank*, Accession No. U65590, Dec. 22, 1997. Definition: "*Homo sapiens* IL-1 receptor antagonist IL-1Ra (IL-1RN) gene, alternatively spliced forms, complete cds."

Bruno Lemaitre, et al., *Cell*, 86:973-983, Sep. 20, 1996. "The Dorsoventral Regulatory Gene Cassette *spätzle/Toll/cactus* Controls the Potent Antifungal Response in Drosophilia Adults".

S.R. Leong, *GenBank*, Accession No. X12497, Mar. 13, 1995. Definition: "Bovine mRNA for interleukin-1 alpha".

Patricia J. Lodi, et al., *Science*, 263:1762-1766, Mar. 25, 1994. "High-Resolution Solution Structure of the β Chemokine hMIP-1β by Multidimensional NMR".

C.R. Maliszewski, *GenBank*, Accession No. X52731, Mar. 31, 1995. Definition: "Pig mRNA for interleukin 1-alpha".

C.J. March, et al., *GenPept*, Accession No. 124297, Oct. 1, 1996. Definition: "Interleukin-1 Alpha Precursor (IL-1 Alpha (Hematopoietin-1)".

M. Marra, et al., *GenBank*, Accesion No. AA030324, Jan. 21, 1997. Definition: "mi08c10.r1 Soares mouse placenta 4NbMP13.5 14.5 Mus musculus cDNA clone 459858 5', mRNA sequence".

M. Marra, et al., *GenBank*, Accession No. W08205, Sep. 5, 1996. Definition: "mb49b11.r1 Soares mouse p3NMF19.5 Mus musculus cDNA clone 332733 5' similar to PIR:A49031 A49031 interleukin 1 receptor antagonist—mouse ;, mRNA sequence".

Y. Masaaki, et al., *GenBank*, Accession No. E01109, Nov. 26, 1996. Definition: "cDNA sequence of human IL-1".

Y. Masaaki et al., *GenBank*, Accession No. E01442, Nov. 26, 1996. Definition: "cDNA encoding human IL-1".

T. Nishida, et al., *GenBank*, Accession No. D00403, Jan. 19, 1992. Definition: "Rat interleukin-1 alpha mRNA, complete cds."

Haruki Okamura, et al., *Nature*, 378:88-91, Nov. 2, 1995. "Cloning of a new cytokine that induces IFN-γ production by T cells".

Joost J. Oppenheim, et al., *Ann. Rev. Immunol.* 9:617-648, 1991. "Properties of the Novel Proinflammatory Supergene 'Intercrine' Cytokine Family".

Helge Rothe, et al., *The Journal of Clinical Investigation*, 99(3):469-474, Feb. 1997. "Active Stage of Autoimmune Diabetes Is Associated with the Expression of a Novel Cytokine, IGIF, Which Is Located Near *Idd2*".

Roger A. Sayle, et al., *TIBS*, 20:374-376, Sep. 1995. "Ramsol: biomolecular graphics for all".

H.F. Sewo, *GenBank*, Accesion No. X56972, May 26, 1992. Definition: "Ovine IL-1 beta mRNA for interleukin-1 beta".

J.L. Telford, et al., *GenBank*, Accession No. X04964, Sep. 16, 1994. Definition: "Murine interleukin-1 beta gene".

K. Totsuka, et al., *GenBank*, Accession No. D63353, Feb. 13, 1997. Definition: "Cynomolgus monkey mRNA for interleukin-1-beta".

S. Ushio, et al., *GenPept*, Accession No. 1405319, Jul. 5, 1996. Definition: "interferon-gamma inducing factor (IGIF)".

K. Zahedi, et al., *GenBank*, Accession No. M74294, Aug. 23, 1991. Definition: "Mouse IL-1rn antagonist protein mRNA, complete cds."

* cited by examiner

```
hIL-1ε    MRGTPGDADGGGRAVYQSMCKPITGTINDLNQQVWTLQGQ-
mIL-1ε    ...EKELRAASPSLRHVQDLSSRVWILQNN-
mIL-18    ...VLSGALCFRMKDSALKVLYLHNNQ
hIL-1RA   ...KSSKMQAFRIWDVNQKTFYLRNNQ                    29
hIL-1γ    ...YFGKLESKLSVIRNLNDQVLFIDQG-NRP
mIL-1γ    ...NFGRLHCTTAVIRNIINDQVLFVDKR--QP
hIL-1β    ...APVRSLNCTLRDSQQKSLVMSGPY
hIL-1α    ...MRIIKYEFILNDALNQSIIRANDQ hIL-1ε    NLVAVPRSDSV---TPVTVAVITCKYPEALEQGRGDPIYLGIQN-PEMCL
mIL-1ε    ILTAVPRKEQT---VPVTITLLPCQYLDTLETNRGDPTYMGVQR-PMSCL
mIL-18    LLAGGLHAEKV--IKGEEISVVPNRALDASL----SPVILGVQG-GSQCL   79
hIL-1RA   LVAGYLQGPNV--NLEEKIDVVPIEP--------HALFLGIHG-GKMCL
hIL-1γ    LFEDMTDSDCRDNAPRTIFIISMYKDSQPRG----MAVTISVKCEKISTL
mIL-1γ    VFEDMTDIDQSASEPQTRLIIYMYKDSEVRG----LAVTLSVKDSKMSTL
hIL-1β    ELKALHLQGQDM-EQQVVFSMSFVQGEESNDK---IPVALGLKE-KNLYL
hIL-1α    YLTAAALHNLD---EAVKFDMGAYKSSKDDAK---ITVILRISK-TQLYV
```

FIG. 2A

```
hIL-1ε     YCEKVGEQPTLQLKEQKIMDLYGQPEPVKPFLFYRAKTGR---TSTLESV
mIL-1ε     FCTKDGEQPVLQLGEGNIMEMYNKKEPVKASLFYHKKSG---TTSTFESA
mIL-1δ     SCGT-EKGPILKLEPVNIMELYLGAKESKSFTFYRRDMG---LTSSFESA
hIL-1RA    SCVKSGDETRLQLEAVNITDLSENRKQDKRFAFIRSDSGP---TTSFESA
hIL-1γ     SCENKIISFKEMNPPDNIKDTK------SDIFFQRSVPGHDNKMQFESS
mIL-1γ     SCKNKIISFEEMDPPENIDDIQ------SDLIFFQKRVPGH-NKMEFESS
hIL-1β     SCVLKDDKPTLQLESVDPKNYPKKKM--EKRFVFNKIEI--NNKLEFESA    129
hIL-1α     TAQD-EDQPVLLKEMPEIPKTITGS--ETNLLFFWETH---GTKNYFTSV hIL-1ε     AFPDWFIASS-K-RDQPIILTSELGKSY----NTAFELNIND
mIL-1ε     AFPGWFIAVCSK-GSCPLILTQELGEIF----ITDFEMIVH
mIL-1δ     AYPGWFLCTSPE-ADQPVRLTQIPEDPAWDAPITDFYFQQCD
hIL-1RA    ACPGWFLCTAME-ADQPVSLTNMPDEGVM---VTKFYFQEDE
hIL-1γ     SYEGYFLACEKERDLFKLILKKEDELGDR---SIMFTVQNED
mIL-1γ     LYEGHFLACQKEDDAFKLILKKDENGDK---SVMFTLTNLHQS
hIL-1β     QFPNWYISTSQA-ENMPVFLGGTKGGQD----ITDFTMQFVSS         171
hIL-1α     AHPNLFIATKQ---DYWVCLAGGPPS------ITDFQILENQA
```

FIG. 2B

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
       (A) LENGTH: 470 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..468

(xi) SEQUENCE DESCRIPTION: SEQ ID NO: 1:

```
ATG ATG GTT CTG AGT GGG GCA CTA TGC TTC CGA ATG AAG GAT TCA GCC        48
Met Met Val Leu Ser Gly Ala Leu Cys Phe Arg Met Lys Asp Ser Ala
 1               5                  10                  15

TTG AAG GTA CTG TAT CTG CAC AAT AAC CAG CTG CTG GCT GGA GGA CTG        96
Leu Lys Val Leu Tyr Leu His Asn Asn Gln Leu Leu Ala Gly Gly Leu
            20                  25                  30

CAC GCA GAG AAG GTC ATT AAA GGT GAG GAG ATC AGT GTT GTC CCA AAT       144
His Ala Glu Lys Val Ile Lys Gly Glu Glu Ile Ser Val Val Pro Asn
        35                  40                  45

CGG GCA CTG GAT GCC AGT CTG TCC CCT GTC ATC CTG GGC GTT CAA GGA       192
Arg Ala Leu Asp Ala Ser Leu Ser Pro Val Ile Leu Gly Val Gln Gly
    50                  55                  60

GGA AGC CAG TGC CTA TCT TGT GGG ACA GAG AAA GGG CCA ATT CTG AAA       240
Gly Ser Gln Cys Leu Ser Cys Gly Thr Glu Lys Gly Pro Ile Leu Lys
65                  70                  75                  80

CTT GAG CCA GTG AAC ATC ATG GAG CTC TAC CTC GGG GCC AAG GAA TCA       288
Leu Glu Pro Val Asn Ile Met Glu Leu Tyr Leu Gly Ala Lys Glu Ser
                85                  90                  95

AAG AGC TTC ACC TTC TAC CGG CGG GAT ATG GGT CTT ACC TCC AGC TTC       336
Lys Ser Phe Thr Phe Tyr Arg Arg Asp Met Gly Leu Thr Ser Ser Phe
            100                 105                 110

GAA TCC GCT GCC TAC CCA GGC TGG TTC CTC TGC ACC TCA CCG GAA GCT       384
Glu Ser Ala Ala Tyr Pro Gly Trp Phe Leu Cys Thr Ser Pro Glu Ala
        115                 120                 125

GAC CAG CCT GTC AGG CTC ACT CAG ATC CCT GAG GAC CCC GCC TGG GAT       432
Asp Gln Pro Val Arg Leu Thr Gln Ile Pro Glu Asp Pro Ala Trp Asp
    130                 135                 140

GCT CCC ATC ACA GAC TTC TAC TTT CAG CAG TGT GAC TA                    470
Ala Pro Ile Thr Asp Phe Tyr Phe Gln Gln Cys Asp
145                 150                 155
```

(2) INFORMATION FOR SEQ ID NO: 2:

(i) SEQUENCE CHARACTERISTICS:
       (A) LENGTH: 156 amino acids
       (B) TYPE: amino acid
       (D) TOPOLOGY: linear (ii) MOLECULE TYPE: protein (xi) SEQUENCE DESCRIPTION: SEQ ID NO: 2:

```
Met Met Val Leu Ser Gly Ala Leu Cys Phe Arg Met Lys Asp Ser Ala
 1               5                  10                  15
```

```
Leu Lys Val Leu Tyr Leu His Asn Asn Gln Leu Leu Ala Gly Gly Leu
            20                  25                  30

His Ala Glu Lys Val Ile Lys Gly Glu Glu Ile Ser Val Val Pro Asn
            35                  40                  45

Arg Ala Leu Asp Ala Ser Leu Ser Pro Val Ile Leu Gly Val Gln Gly
 50                  55                  60

Gly Ser Gln Cys Leu Ser Cys Gly Thr Glu Lys Gly Pro Ile Leu Lys
 65                  70                  75                  80

Leu Glu Pro Val Asn Ile Met Glu Leu Tyr Leu Gly Ala Lys Glu Ser
                85                  90                  95

Lys Ser Phe Thr Phe Tyr Arg Arg Asp Met Gly Leu Thr Ser Ser Phe
            100                 105                 110

Glu Ser Ala Ala Tyr Pro Gly Trp Phe Leu Cys Thr Ser Pro Glu Ala
            115                 120                 125

Asp Gln Pro Val Arg Leu Thr Gln Ile Pro Glu Asp Pro Ala Trp Asp
130                 135                 140

Ala Pro Ile Thr Asp Phe Tyr Phe Gln Gln Cys Asp
145                 150                 155
```

(2) INFORMATION FOR SEQ ID NO: 3:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..216

(xi) SEQUENCE DESCRIPTION: SEQ ID NO: 3:

```
TTC CAG GAA GGG AAC ATA ATG GAA ATG TAC AAC AAA AAG GAA CCT GTA        48
Phe Gln Glu Gly Asn Ile Met Glu Met Tyr Asn Lys Lys Glu Pro Val
 1               5                  10                  15

AAA GCC TCT CTC TTC TAT CAC AAG AAG AGT GGT ACA ACC TCT ACA TTT        96
Lys Ala Ser Leu Phe Tyr His Lys Lys Ser Gly Thr Thr Ser Thr Phe
            20                  25                  30

GAG TCT GCA GCC TTC CCT GGT TGG TTC ATC GCT GTC TGC TCT AAA GGG       144
Glu Ser Ala Ala Phe Pro Gly Trp Phe Ile Ala Val Cys Ser Lys Gly
            35                  40                  45

AGC TGC CCA CTC ATT CTG ACC CAA GAA CTG GGG GAA ATC TTC ATC ACT       192
Ser Cys Pro Leu Ile Leu Thr Gln Glu Leu Gly Glu Ile Phe Ile Thr
 50                  55                  60

GAC TTC GAG ATG ATT GTG GTA CAT TAA                                    219
Asp Phe Glu Met Ile Val Val His
 65                  70
```

(2) INFORMATION FOR SEQ ID NO: 4:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 4:

```
Phe Gln Glu Gly Asn Ile Met Glu Met Tyr Asn Lys Lys Glu Pro Val
 1               5                  10                  15
```

```
            Lys Ala Ser Leu Phe Tyr His Lys Lys Ser Gly Thr Thr Ser Thr Phe
                         20                  25                  30

Glu Ser Ala Ala Phe Pro Gly Trp Phe Ile Ala Val Cys Ser Lys Gly
                         35                  40                  45

Ser Cys Pro Leu Ile Leu Thr Gln Glu Leu Gly Glu Ile Phe Ile Thr
                         50                  55                  60

Asp Phe Glu Met Ile Val Val His
            65                  70

(2) INFORMATION FOR SEQ ID NO: 5:

(i) SEQUENCE CHARACTERISTICS:
        (A) LENGTH: 809 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 90..569

(xi) SEQUENCE DESCRIPTION: SEQ ID NO: 5:

GAATTCGGCA CGAGTGTAGT GTGCAGACAC ATTCCTTATT CAATCAGGGT CAATCTGCAG        60

ATTGGCAGCT CAGGAACAAC ATCACCATA ATG AAT AAG GAG AAA GAA CTA AGA         113
                               Met Asn Lys Glu Lys Glu Leu Arg
                                 1               5

GCA GCA TCA CCT TCG CTT AGA CAT GTT CAG GAT CTT AGT AGT CGT GTG         161
Ala Ala Ser Pro Ser Leu Arg His Val Gln Asp Leu Ser Ser Arg Val
             10                  15                  20

TGG ATC CTG CAG AAC AAT ATC CTC ACT GCA GTC CCA AGG AAA GAG CAA         209
Trp Ile Leu Gln Asn Asn Ile Leu Thr Ala Val Pro Arg Lys Glu Gln
 25                  30                  35                  40

ACA GTT CCA GTC ACT ATT ACC TTG CTC CCA TGC CAA TAT CTG GAC ACT         257
Thr Val Pro Val Thr Ile Thr Leu Leu Pro Cys Gln Tyr Leu Asp Thr
                 45                  50                  55

CTT GAG ACG AAC AGG GGG GAT CCC ACG TAC ATG GGA GTG CAA AGG CCG         305
Leu Glu Thr Asn Arg Gly Asp Pro Thr Tyr Met Gly Val Gln Arg Pro
             60                  65                  70

ATG AGC TGC CTG TTC TGC ACA AAG GAT GGG GAG CAG CCT GTG CTA CAG         353
Met Ser Cys Leu Phe Cys Thr Lys Asp Gly Glu Gln Pro Val Leu Gln
         75                  80                  85

CTT GGG GAA GGG AAC ATA ATG GAA ATG TAC AAC AAA AAG GAA CCT GTA         401
Leu Gly Glu Gly Asn Ile Met Glu Met Tyr Asn Lys Lys Glu Pro Val
     90                  95                 100

AAA GCC TCT CTC TTC TAT CAC AAG AAG AGT GGT ACA ACC TCT ACA TTT         449
Lys Ala Ser Leu Phe Tyr His Lys Lys Ser Gly Thr Thr Ser Thr Phe
105                 110                 115                 120

GAG TCT GCA GCC TTC CCT GGT TGG TTC ATC GCT GTC TGC TCT AAA GGG         497
Glu Ser Ala Ala Phe Pro Gly Trp Phe Ile Ala Val Cys Ser Lys Gly
                125                 130                 135

AGC TGC CCA CTC ATT CTG ACC CAA GAA CTG GGG GAA ATC TTC ATC ACT         545
Ser Cys Pro Leu Ile Leu Thr Gln Glu Leu Gly Glu Ile Phe Ile Thr
            140                 145                 150

GAC TTC GAG ATG ATT GTG GTA CAT TAAGGTTTTT AGACACATTG CTCTGTGGCA        599
Asp Phe Glu Met Ile Val Val His
            155                 160

CTCTCTCAAG ATTTCTTGGA TTCTAACAAG AAGCAATCAA AGACACCCCT AACAAAATGG       659

AAGACTGAAA AGAAAGCTGA GCCCTCCCTG GGCTGTTTTT CCTTGGTGGT GAATCAGATG       719
```

```
CAGAACATCT TACCATGTTT TCATCCAAAG CATTTACTGT TGGTTTTTAC AAGGAGTGAA      779

TTTTTTAAAA TAAAATCATT TATCTCATAA                                      809
```

(2) INFORMATION FOR SEQ ID NO: 6:

(i) SEQUENCE CHARACTERISTICS:
        (A) LENGTH: 160 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Asn Lys Glu Lys Glu Leu Arg Ala Ala Ser Pro Ser Leu Arg His
 1               5                  10                  15

Val Gln Asp Leu Ser Ser Arg Val Trp Ile Leu Gln Asn Asn Ile Leu
             20                  25                  30

Thr Ala Val Pro Arg Lys Glu Gln Thr Val Pro Val Thr Ile Thr Leu
         35                  40                  45

Leu Pro Cys Gln Tyr Leu Asp Thr Leu Glu Thr Asn Arg Gly Asp Pro
     50                  55                  60

Thr Tyr Met Gly Val Gln Arg Pro Met Ser Cys Leu Phe Cys Thr Lys
65                  70                  75                  80

Asp Gly Glu Gln Pro Val Leu Gln Leu Gly Glu Gly Asn Ile Met Glu
                 85                  90                  95

Met Tyr Asn Lys Lys Glu Pro Val Lys Ala Ser Leu Phe Tyr His Lys
            100                 105                 110

Lys Ser Gly Thr Thr Ser Thr Phe Glu Ser Ala Ala Phe Pro Gly Trp
        115                 120                 125

Phe Ile Ala Val Cys Ser Lys Gly Ser Cys Pro Leu Ile Leu Thr Gln
    130                 135                 140

Glu Leu Gly Glu Ile Phe Ile Thr Asp Phe Glu Met Ile Val Val His
145                 150                 155                 160
```

(2) INFORMATION FOR SEQ ID NO: 7:

(i) SEQUENCE CHARACTERISTICS:
        (A) LENGTH: 177 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 7:

```
Met Glu Ile Cys Arg Gly Leu Arg Ser His Leu Ile Thr Leu Leu Leu
 1               5                  10                  15

Phe Leu Phe His Ser Glu Thr Ile Cys Arg Pro Ser Gly Arg Lys Ser
             20                  25                  30

Ser Lys Met Gln Ala Phe Arg Ile Trp Asp Val Asn Gln Lys Thr Phe
         35                  40                  45

Tyr Leu Arg Asn Asn Gln Leu Val Ala Gly Tyr Leu Gln Gly Pro Asn
     50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                 85                  90                  95

Ser Gly Asp Glu Thr Arg Leu Gln Leu Glu Ala Val Asn Ile Thr Asp
            100                 105                 110
```

```
Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
        130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

(2) INFORMATION FOR SEQ ID NO: 8:

(i) SEQUENCE CHARACTERISTICS:
        (A) LENGTH: 193 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 8:

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

(2) INFORMATION FOR SEQ ID NO: 9:

(i) SEQUENCE CHARACTERISTICS:
        (A) LENGTH: 192 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 9:

```
Met Ala Ala Met Ser Glu Asp Ser Cys Val Asn Phe Lys Glu Met Met
1               5                   10                  15

Phe Ile Asp Asn Thr Leu Tyr Phe Ile Pro Glu Asn Gly Asp Leu
            20                  25                  30

Glu Ser Asp Asn Phe Gly Arg Leu His Cys Thr Thr Ala Val Ile Arg
        35                  40                  45

Asn Ile Asn Asp Gln Val Leu Phe Val Asp Lys Arg Gln Pro Val Phe
50                      55                  60

Glu Asp Met Thr Asp Ile Asp Gln Ser Ala Ser Glu Pro Gln Thr Arg
65                      70                  75                  80

Leu Ile Ile Tyr Met Tyr Lys Asp Ser Glu Val Arg Gly Leu Ala Val
                85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
            115                 120                 125

Ile Gln Ser Asp Leu Ile Phe Phe Gln Lys Arg Val Pro Gly His Asn
130                 135                 140

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175

Asn Gly Asp Lys Ser Val Met Phe Thr Leu Thr Asn Leu His Gln Ser
            180                 185                 190

(2) INFORMATION FOR SEQ ID NO: 10:

(i) SEQUENCE CHARACTERISTICS:
        (A) LENGTH: 269 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 10:

Met Ala Glu Val Pro Lys Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
50                      55                  60

Ala Ser Val Val Val Ala Met Asp Lys Leu Arg Lys Met Leu Val Pro
65                      70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160
```

```
Ser Phe Val Gln Gly Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
            210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
                260                 265
```

(2) INFORMATION FOR SEQ ID NO: 11:

(i) SEQUENCE CHARACTERISTICS:
        (A) LENGTH: 271 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 11:

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
                20                  25                  30

Lys Ser Phe Tyr His Val Ser Tyr Gly Pro Leu His Glu Gly Cys Met
            35                  40                  45

Asp Gln Ser Val Ser Leu Ser Ile Ser Glu Thr Ser Lys Thr Ser Lys
50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Val Lys Tyr Asn Phe Met Arg
            115                 120                 125

Ile Ile Lys Tyr Glu Phe Ile Leu Asn Asp Ala Leu Asn Gln Ser Ile
            130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
            210                 215                 220

Trp Glu Thr His Gly Thr Lys Asn Tyr Phe Thr Ser Val Ala His Pro
225                 230                 235                 240
```

```
Asn Leu Phe Ile Ala Thr Lys Gln Asp Tyr Trp Val Cys Leu Ala Gly
            245                 250                 255

Gly Pro Pro Ser Ile Thr Asp Phe Gln Ile Leu Glu Asn Gln Ala
            260                 265                 270
```

(2) INFORMATION FOR SEQ ID NO: 12:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..504

(ix) FEATURE:
        (A) NAME/KEY: misc_feature
        (B) LOCATION: 144
        (D) OTHER INFORMATION: /note= "nucleotide 144 designated
            G, may be G or T"

(ix) FEATURE:
        (A) NAME/KEY: misc_feature
        (B) LOCATION: 451
        (D) OTHER INFORMATION: /note= "nucleotide 451 designated
            C, may be C or T"

(ix) FEATURE:
        (A) NAME/KEY: misc_feature
        (B) LOCATION: 469
        (D) OTHER INFORMATION: /note= "nucleotide 469 designated
            C, may be A, C, G, or T"

(xi) SEQUENCE DESCRIPTION: SEQ ID NO: 12:

```
ATG AGA GGC ACT CCA GGA GAC GCT GAT GGT GGA GGA AGG GCC GTC TAT        48
Met Arg Gly Thr Pro Gly Asp Ala Asp Gly Gly Gly Arg Ala Val Tyr
 1               5                  10                  15

CAA TCA ATG TGT AAA CCT ATT ACT GGG ACT ATT AAT GAT TTG AAT CAG        96
Gln Ser Met Cys Lys Pro Ile Thr Gly Thr Ile Asn Asp Leu Asn Gln
                20                  25                  30

CAA GTG TGG ACC CTT CAG GGT CAG AAC CTT GTG GCA GTT CCA CGA AGG       144
Gln Val Trp Thr Leu Gln Gly Gln Asn Leu Val Ala Val Pro Arg Arg
            35                  40                  45

ACC AGT GTG ACC CCA GTC ACT GTT GCT GTT ATC ACA TGC AAG TAT CCA       192
Thr Ser Val Thr Pro Val Thr Val Ala Val Ile Thr Cys Lys Tyr Pro
 50                  55                  60

GAG GCT CTT GAG CAA GGC AGA GGG GAT CCC ATT TAT TTG GGA ATC CAG       240
Glu Ala Leu Glu Gln Gly Arg Gly Asp Pro Ile Tyr Leu Gly Ile Gln
 65                  70                  75                  80

AAT CCA GAA ATG TGT TTG TAT TGT GAG AAG GTT GGA GAA CAG CCC ACA       288
Asn Pro Glu Met Cys Leu Tyr Cys Glu Lys Val Gly Glu Gln Pro Thr
                85                  90                  95

TTG CAG CTA AAA GAG CAG AAG ATC ATG GAT CTG TAT GGC CAA CCC GAG       336
Leu Gln Leu Lys Glu Gln Lys Ile Met Asp Leu Tyr Gly Gln Pro Glu
            100                 105                 110

CCC GTG AAA CCC TTC CTT TTC TAC CGT GCC AAG ACT GGT AGG ACC TCC       384
Pro Val Lys Pro Phe Leu Phe Tyr Arg Ala Lys Thr Gly Arg Thr Ser
        115                 120                 125

ACC CTT GAG TCT GTG GCC TTC CCG GAC TGG TTC ATT GCC TCC TCC AAG       432
Thr Leu Glu Ser Val Ala Phe Pro Asp Trp Phe Ile Ala Ser Ser Lys
130                 135                 140

GGA GAC CAG CCC ATC ATT CTG ACT TCA GAA CTT TGG CAG TCA TAC AAC       480
Gly Asp Gln Pro Ile Ile Leu Thr Ser Glu Leu Trp Gln Ser Tyr Asn
```

```
                145                 150                 155                 160
ACT GCC TTT GAA TTA AAT ATT AAT G                                            505
Thr Ala Phe Glu Leu Asn Ile Asn
                165
```

(2) INFORMATION FOR SEQ ID NO: 13:

(i) SEQUENCE CHARACTERISTICS:
        (A) LENGTH: 168 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Arg Gly Thr Pro Gly Asp Ala Asp Gly Gly Gly Arg Ala Val Tyr
 1               5                  10                  15

Gln Ser Met Cys Lys Pro Ile Thr Gly Thr Ile Asn Asp Leu Asn Gln
             20                  25                  30

Gln Val Trp Thr Leu Gln Gly Gln Asn Leu Val Ala Val Pro Arg Arg
         35                  40                  45

Thr Ser Val Thr Pro Val Thr Val Ala Val Ile Thr Cys Lys Tyr Pro
 50                  55                  60

Glu Ala Leu Glu Gln Gly Arg Gly Asp Pro Ile Tyr Leu Gly Ile Gln
 65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
        115                 120                 125

Thr Leu Glu Ser Val Ala Phe Pro Asp Trp Phe Ile Ala Ser Ser Lys
130                 135                 140

Gly Asp Gln Pro Ile Ile Leu Thr Ser Glu Leu Trp Gln Ser Tyr Asn
145                 150                 155                 160

Thr Ala Phe Glu Leu Asn Ile Asn
                165
```

(2) INFORMATION FOR SEQ ID NO: 14:

(i) SEQUENCE CHARACTERISTICS:
        (A) LENGTH: 1195 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 67..573

(xi) SEQUENCE DESCRIPTION: SEQ ID NO: 14:

```
CCACGATTCA GTCCCTGGA CTGTAGATAA AGACCCTTTC TTGCCAGGTG CTGAGACAAC      60

CACACT ATG AGA GGC ACT CCA GGA GAC GCT GAT GGT GGA GGA AGG GCC       108
       Met Arg Gly Thr Pro Gly Asp Ala Asp Gly Gly Gly Arg Ala
        1               5                  10

GTC TAT CAA TCA ATG TGT AAA CCT ATT ACT GGG ACT ATT AAT GAT TTG      156
Val Tyr Gln Ser Met Cys Lys Pro Ile Thr Gly Thr Ile Asn Asp Leu
 15                  20                  25                  30

AAT CAG CAA GTG TGG ACC CTT CAG GGT CAG AAC CTT GTG GCA GTT CCA      204
```

-continued

```
Asn Gln Gln Val Trp Thr Leu Gln Gly Gln Asn Leu Val Ala Val Pro
             35                  40                  45

CGA AGT GAC AGT GTG ACC CCA GTC ACT GTT GCT GTT ATC ACA TGC AAG      252
Arg Ser Asp Ser Val Thr Pro Val Thr Val Ala Val Ile Thr Cys Lys
             50                  55                  60

TAT CCA GAG GCT CTT GAG CAA GGC AGA GGG GAT CCC ATT TAT TTG GGA      300
Tyr Pro Glu Ala Leu Glu Gln Gly Arg Gly Asp Pro Ile Tyr Leu Gly
             65                  70                  75

ATC CAG AAT CCA GAA ATG TGT TTG TAT TGT GAG AAG GTT GGA GAA CAG      348
Ile Gln Asn Pro Glu Met Cys Leu Tyr Cys Glu Lys Val Gly Glu Gln
         80                  85                  90

CCC ACA TTG CAG CTA AAA GAG CAG AAG ATC ATG GAT CTG TAT GGC CAA      396
Pro Thr Leu Gln Leu Lys Glu Gln Lys Ile Met Asp Leu Tyr Gly Gln
 95             100                 105                 110

CCC GAG CCC GTG AAA CCC TTC CTT TTC TAC CGT GCC AAG ACT GGT AGG      444
Pro Glu Pro Val Lys Pro Phe Leu Phe Tyr Arg Ala Lys Thr Gly Arg
                115                 120                 125

ACC TCC ACC CTT GAG TCT GTG GCC TTC CCG GAC TGG TTC ATT GCC TCC      492
Thr Ser Thr Leu Glu Ser Val Ala Phe Pro Asp Trp Phe Ile Ala Ser
                130                 135                 140

TCC AAG AGA GAC CAG CCC ATC ATT CTG ACT TCA GAA CTT GGG AAG TCA      540
Ser Lys Arg Asp Gln Pro Ile Ile Leu Thr Ser Glu Leu Gly Lys Ser
            145                 150                 155

TAC AAC ACT GCC TTT GAA TTA AAT ATA AAT GAC TGAACTCAGC CTAGAGGTGG    593
Tyr Asn Thr Ala Phe Glu Leu Asn Ile Asn Asp
            160                 165

CAGCTTGGTC TTTGTCTTAA AGTTTCTGGT TCCCAATGTG TTTTCGTCTA CATTTTCTTA    653

GTGTCATTTT CACGCTGGTG CTGAGACAGG GGCAAGGCTG CTGTTATCAT CTCATTTTAT    713

AATGAAGAAG AAGCAATTAC TTCATAGCAA CTGAAGAACA GGATGTGGCC TCAGAAGCAG    773

GAGAGCTGGG TGGTATAAGG CTGTCCTCTC AAGCTGGTGC TGTGTAGGCC ACAAGGCATC    833

TGCATGAGTG ACTTTAAGAC TCAAAGACCA AACACTGAGC TTTCTTCTAG GGGTGGGTAT    893

GAAGATGCTT CAGAGCTCAT GCGCGTTACC CACGATGGCA TGACTAGCAC AGAGCTGATC    953

TCTGTTTCTG TTTTGCTTTA TTCCCTCTTG GGATGATATC ATCCAGTCTT TATATGTTGC   1013

CAATATACCT CATTGTGTGT AATAGAACCT TCTTAGCATT AAGACCTTGT AAACAAAAAT   1073

AATTCTTGTG TTAAGTTAAA TCATTTTTGT CCTAATTGTA ATGTGTAATC TTAAAGTTAA   1133

ATAAACTTTG TGTATTTATA TAATAATAAA GCTAAAACTG ATATAAAAAA AAAAAAAAA    1193

AA                                                                  1195
```

(2) INFORMATION FOR SEQ ID NO: 15:

(i) SEQUENCE CHARACTERISTICS:
        (A) LENGTH: 169 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Arg Gly Thr Pro Gly Asp Ala Asp Gly Gly Arg Ala Val Tyr
 1               5                  10                  15

Gln Ser Met Cys Lys Pro Ile Thr Gly Thr Ile Asn Asp Leu Asn Gln
             20                  25                  30

Gln Val Trp Thr Leu Gln Gly Gln Asn Leu Val Ala Val Pro Arg Ser
             35                  40                  45

Asp Ser Val Thr Pro Val Thr Val Ala Val Ile Thr Cys Lys Tyr Pro
```

-continued

```
                50                  55                  60
Glu Ala Leu Glu Gln Gly Arg Gly Asp Pro Ile Tyr Leu Gly Ile Gln
 65                  70                  75                  80

Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
                100                 105                 110

Pro Val Lys Pro Phe Leu Phe Tyr Arg Ala Lys Thr Gly Arg Thr Ser
            115                 120                 125

Thr Leu Glu Ser Val Ala Phe Pro Asp Trp Phe Ile Ala Ser Ser Lys
        130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```

MAMMALIAN CYTOKINES; RELATED REAGENTS AND METHODS

This application is a divisional of U.S. Ser. No. 09/130,972, filed Aug. 7, 1998, which is a continuation application of copending U.S. Ser. No. 09/097,976, filed Jun. 16, 1998 now abandoned; which is a continuation application of then copending U.S. Ser. No. 09/062,866, filed Apr. 20, 1998 now abandoned; which was a conversion to a U.S. Utility Patent Application of Provisional U.S. Pat. applications U.S. Ser. No. 60/044,165, filed Apr. 21, 1997, and U.S. Ser. No. 60/055,111, filed Aug. 6, 1997; each of which is incorporated herein by reference.

FIELD OF THE INVENTION

The present invention relates to compositions and methods for affecting mammalian physiology, including morphogenesis or immune system function. In particular, it provides nucleic acids, proteins, and antibodies which regulate development and/or the immune system. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotent hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

The interleukin-1 family of proteins includes the IL-1α, the IL-1β, the IL-1RA, and recently the IL-1γ (also designated Interferon-Gamma Inducing Factor, IGIF). This related family of genes have been implicated in a broad range of biological functions. See Dinarello (1994) *FASEB J.* 8:1314–1325; Dinarello (1991) *Blood* 77:1627–1652; and Okamura, et al. (1995) *Nature* 378:88–91.

In addition, various growth and regulatory factors exist which modulate morphogenetic development. This includes, e.g., the Toll ligands, which signal through binding to receptors which share structural, and mechanistic, features characteristic of the IL-1 receptors. See, e.g., Lemaitre, et al. (1996) *Cell* 86:973–983; and Belvin and Anderson (1996) *Ann. Rev. Cell & Develop. Biol.* 12:393–416.

From the foregoing, it is evident that the discovery and development of new soluble proteins, including ones similar to lymphokines, should contribute to new therapies for a wide range of degenerative or abnormal conditions which directly or indirectly involve development, differentiation, or function, e.g., of the immune system and/or hematopoietic cells. In particular, the discovery and understanding of novel lymphokine-like molecules which enhance or potentiate the beneficial activities of other lymphokines would be highly advantageous. The present invention provides new interleukin-1 like compositions and related compounds, and methods for their use.

SUMMARY OF THE INVENTION

The present invention is based on the discovery, purification, and characterization of the biological activities of two novel mammalian, e.g., rodent, interleukin-1 like molecules, designated interleukin-1δ (IL-1δ) and interleukin-1ε (IL-1ε). Both IL-1δ and IL-1ε exhibit both structural and sequence similarity, e.g., by homology comparison, to known members of the IL-1 family of molecules. A primate, e.g., human counterpart IL-1ε is also described.

In a first aspect, the invention provides IL-1δ and IL-1ε polypeptides and nucleic acids coding for these polypeptides, methods for their production and use. The nucleic acids of the invention are characterized, in part, by their homology to cloned complementary DNA (cDNA)

sequences enclosed herein, and/or by functional assays for IL-1δ or IL-1ε activity applied to the polypeptides, which are typically encoded by these nucleic acids. Methods for modulating or intervening in the control of an immune response are also provided by the use of IL-1δ or IL-1ε either singly or in combination with other molecules.

The biological functions of the new IL-1δ or IL-1ε gene products should be similar to, and may well share receptors or portions of the signaling pathways used by known IL-1 family members. Equivalent vectors may be constructed by using polymerase chain reaction (PCR) techniques and sequences of the inserts.

In another aspect, the present invention provides isolated or recombinant IL-1δ or IL-1ε polypeptides that specifically bind polyclonal antibodies generated against a 12 consecutive amino residues of a defined amino acid segment (i.e., SEQ ID NO: 2, 6, 13, or 15). These IL-1δ or IL-1ε polypeptides are further defined by comprising a select sequence of additional defined amino acids. Further, in another embodiment, fusion proteins comprising IL-1δ or IL-1ε polypeptides are provided. In still another aspect, there are provided variants, including fragments, natural alleles, labels, and modifications of the IL-1δ or IL-1ε polypeptides. Also provided are the nucleic acids encoding such fragments, variants or modified polypeptides.

Certain polypeptide embodiments include an isolated or recombinant polypeptide that: A) specifically binds polyclonal antibodies generated against a 12 consecutive amino acid segment of SEQ ID NO: 2; and comprises at least one sequence selected from: LeuCysPheArgMetLyp (residues 8–14 of SEQ ID NO:2); ValLeuTyrLeuHisAsn (residues 19–24 of SEQ ID NO:2); GlnLeuLeuAlaGly (residues 26–30 of SEQ ID NO:2); IleSerValValProAsn (residues 43–48 of SEQ ID NO:2); SerProValIleLeuGlyVal (residues 56–62 of SEQ ID NO:2); GlnCysLeuSerCysGlyThr (residues 67–73 of SEQ ID NO:2); ProIleLeuLysLeuGlu (residues 77–82 of SEQ ID NO:2); PheTyrArgArgAspMetGly (residues 101–107 of SEQ ID NO:2); LeuThrSerSerPheGluSer (residues 108–114 of SEQ ID NO:2); PheLeuCysThrSer (residues 121–125 of SEQ ID NO:2); GlnProValArgLeuThr (residues 130–135 of SEQ ID NO:2); PheTyrPheGlnGln (residues 150–154 of SEQ ID NO:2); ArgAlaLeuAspAlaSerLeu (residues 49–55 of SEQ ID NO:2); or GlyLeuHisAlaGluLysVal (residues 31–37 of SEQ ID NO:2); or B) specifically binds polyclonal antibodies generated against a 12 consecutive amino acid segment of SEQ ID NO: 6, 13, or 15; and comprises at least one sequence selected from: SerLeuArgHisValGlnAsp (residues 13–19 of SEQ ID NO:6); ValTrpIleLeuGlnAsn (residues 24–29 of SEQ ID NO:6); IleLeuThrAlaVal (residues 31–35 of SEQ ID NO:6); IleThrLeuLeuProCys (residues 46–51 of SEQ ID NO:6); AspProThrTyrMetGlyVal (residues 63–69 of SEQ ID NO:6); SerCysLeuPheCysThrLys (residues 74–80 of SEQ ID NO:6); ProValLeuGlnLeuGly (residues 85–90 of SEQ ID NO:6); PheTyrHisLysLysSerGly (residues 109–115 of SEQ ID NO:6); ThrThrSerThrPheGluSer (residues 116–122 of SEQ ID NO:6); PheIleAlaValCys (residues 129–133 of SEQ ID NO:6); CysProLeuIleLeuThr (residues 138–143 of SEQ ID NO:6); PheGluMetIleVal (residues 154–158 of SEQ ID NO:6); GlnAspLeuSer (residues 18–21 of SEQ ID NO:6); ValProArgLysGluGlnThrVal (residues 35–42 of SEQ ID NO:6); SerLysGlySerCysPrO (residues 134–139 of SEQ ID NO:6); ArgAlaAlaSer (residues 8–11 of SEQ ID NO:6); ProCysGlnTyrLeuAspThrLeuGlu (residues 50–58 of SEQ ID NO:6); and SerGlyThrThr (residues 114–117 of SEQ ID NO:6); or ITGTIND (residues 23–29 of SEQ ID NO:13); VWTLQG (residues 34–39 of SEQ ID NO:13); NLVAV (residues 41–45 of SEQ ID NO:13); VAVITQ (residues 56–61 of SEQ ID NO:13); DPIYLGI (residues 73–79 of SEQ ID NO:13); MCLYCEK (residues 84–90 of SEQ ID NO:13); PTLQLK (residues 95–100 of SEQ ID NO:13); FYRAKTG (residues 119–125 of SEQ ID NO:13); RTSTLES (residues 126–132 of SEQ ID NO:13); FIASS (residues 139–143 of SEQ ID NO:13); QPIILT (residues 147–152 of SEQ ID NO:13); FELNI (residues 163–167 of SEQ ID NO:13); SMCK (residues 18–21 of SEQ ID NO:13); NDLN (residues 28–31 of SEQ ID NO:13); [VPR(R/S)TSVT] VPRRTSVT (residues 45–51 of SEQ ID NO:13); TCKYPEALE (residues 60–68 of SEQ ID NO:13); TGRT (residues 124–127 of SEQ ID NO:13); or SKGDQP (residues 143–148 of SEQ ID NO:13), or VPRSDSVT (residues 45–52 of SEQ ID NO:15); SKRDQP (residues 143–148 of SEQ ID NO:15). Preferred embodiments include such a polypeptide: wherein the polypeptide comprises a plurality of the described sequences. Preferably the 12 consecutive amino acid segment comes from an IL-1δ sequence (see SEQ ID NO: 2): LeuCysPheArgMetLysAspSerAlaLeuLysValLeuTyrLeuHisAsnAsn (residues 8–25 of SEQ ID NO:2); IleSerValValProAsnArgAlaLeuAspAlaSerLeuSerProValIleLeuGlyValGln (residues 43–63 of SEQ ID NO:2); SerProValIleLeuGlyValGlnGlyGlySerGlnCys (residues 56–68 of SEQ ID NO:2); ProIleLeuLysLeuGluProValAsnIleMetGluLeu (residues 77–89 of SEQ ID NO:2); ThrSerSerPheGluSerAlaAlaTyrProGlyTrpPhe (residues 109–121 of SEQ ID NO:2); PheLeuCysThrSerProGluAlaAspGlnProVal (residues 121–132 of SEQ ID NO:2); ThrGlnIleProGluAspProAlaTrpAspAlaProIle (residues 135–147 of SEQ ID NO:2); or ThrSerSerPheGluSerAlaAlaTyrProGlyTrpPhe (residues 109–121 of SEQ ID NO:2); or a rodent IL-1ε sequence (see SEQ ID NO: 6): ArgAlaAlaSerProSerLeuArgHisValGlnAspLeu (residues 8–20 of SEQ ID NO:6); SerSerArgValTrpIleLeuGlnAsnAsnIleLeu (residues 21–32 of SEQ ID NO:6); ProValThrIleThrLeuLeuProCysGlnTyrLeu (residues 43–54 of SEQ ID NO:6); GlyValGlnArgProMetSerCysLeuPheCysThr (residues 68–79 of SEQ ID NO:6); PheCysThrLysAspGlyGluGlnProValLeuGlnLeu (residues 77–89 of SEQ ID NO:6); ThrSerThrPheGluSerAlaAlaPheProGlyTrpPhe (residues 117–129 of SEQ ID NO:6); or CysSerLysGlySerCysProLeuIleLeuThrGln (residues 134–144 of SEQ ID NO:6); or a primate IL-Iε sequence (see SEQ ID NO: 13 or 15): SMCKPITGTINDL (residues 18–30 of SEQ ID NO:13); NQQVWTLQGQNL (residues 31–42 of SEQ ID NO:13); PVTVAVITCKYP (residues 53–64 SEQ ID NO:13); GIQNPEMCLYCE (residues 78–89 of SEQ ID NO:13); YCEKVGEQPTLQL (residues 87–99 of SEQ ID NO:13); TSTLESVAFPDWF (residues 127–139 of SEQ ID NO:13); SKGDQPIILTSE (residues 143–154 of SEQ ID NO:13); SKRDQPIILTSE (residues 143–154 of SEQ ID NO:15);or GKSYNTAFELNIND (residues 156–169 of SEQ ID NO:15).

In particularly preferred embodiments, the: polypeptide: comprises a mature protein; lacks a post-translational modification; is from a rodent, including a mouse; is from a primate, including a human; is a natural allelic variant of IL-1δ or IL-1ε; has a length at least about 30 amino acids; exhibits at least two non-overlapping epitopes that are specific for a rodent IL-1δ; exhibits a sequence identity over a length of at least about 20 amino acids to SEQ ID NO: 2; exhibits at least two non-overlapping epitopes which are specific for a rodent or primate IL-1ε; exhibits a sequence identity over a length of at least about 20 amino acids to SEQ ID NO: 6, 13, or 15; is glycosylated; has a molecular weight of at least 10 kD with natural glycosylation; is a synthetic polypeptide; is attached to a solid substrate; is conjugated to another chemical moiety; is a 5-fold or less substitution from natural sequence; or is a deletion or insertion variant from a natural sequence. Other preferred embodiments include, e.g., a soluble polypeptide comprising: a sterile polypeptide; the sterile polypeptide and a carrier, wherein the carrier is: an aqueous compound, including water, saline, and/or buffer; and/or formulated for oral, rectal, nasal, topical, or parenteral administration. A fusion protein embodiment includes one having a polypeptide sequence as described, further comprising: a mature protein; a detection or purification tag, including a FLAG, His6, or Ig sequence; or sequence of another cytokine or chemokine.

Kit embodiments includes those comprising a protein or polypeptide as described, and: a compartment comprising the protein or polypeptide; and/or instructions for use or disposal of reagents in the kit.

Other embodiments include pharmaceutical compositions comprising a sterile IL-1δ or IL-1ε protein or peptide with a suitable carrier for use in various administrations.

The invention also provides a binding compound comprising an antigen binding site from an antibody, which specifically binds to IL-1δ or IL-1ε protein or polypeptide sequence. Various preferred binding compounds comprise an antigen binding site from an antibody, which specifically binds to a mature protein of a polypeptide, as described, wherein: the mature protein is an IL-1δ or IL-1ε protein; the binding compound is an Fv, Fab, or Fab2 fragment; the binding compound is conjugated to another chemical moiety; or the antibody: is raised against a 12 consecutive amino acid segment of SEQ ID NO: 2, 6, 13, or 15; is raised against a mature IL-1δ or IL-1ε protein; is raised to a purified rodent IL-1δ or IL-L1ε; is raised to a purified primate IL-1ε; is immunoselected; is a polyclonal antibody; binds to a denatured IL-1δ or IL-1ε; exhibits a Kd to antigen of at least 30 μM; is attached to a solid substrate, including a bead or plastic membrane; is in a sterile composition; or is detectably labeled, including a radioactive or fluorescent label.

Other binding compounds include those comprising an antigen binding portion from an antibody, which specifically binds to: a rodent protein, as described, wherein: the protein is a murine protein; the binding compound is an Fv, Fab, or Fab2 fragment; the binding compound is conjugated to another chemical moiety; or the antibody: is raised against a peptide sequence of a mature polypeptide comprising a 12 consecutive amino acid segment of SEQ ID NO: 2 or SEQ ID NO: 6, 13, or 15; is raised against a mature rodent IL-1δ or IL-1ε; is raised to a purified rodent IL-1δ or IL-1ε; is raied to a purified primate IL-1ε; is immunoselected; is a polyclonal antibody; binds to a denatured rodent IL-1δ or IL-1ε; binds to a denatured primate IL-1ε; exhibits a Kd to antigen of at least 30 μM; is attached to a solid substrate, including a bead or plastic membrane; is in a sterile composition; or is detectably labeled, including a radioactive or fluorescent label. Methods are provided using such binding compounds, e.g., methods of: making an antibody, as described, comprising immunizing an immune system with an immunogenic amount of: a rodent IL-1δ polypeptide; a peptide sequence comprising a 12 consecutive amino acid segment of SEQ ID NO: 2; a rodent or primate IL-1ε polypeptide; a peptide sequence comprising a 12 consecutive amino acid segment of SEQ ID NO: 6, 13, or 15; thereby causing the antibody to be produced; or producing an antigen:antibody complex, comprising contacting: a rodent IL-1δ protein or peptide with an antibody, as described, or a rodent or primate IL-1ε protein or peptide with an antibody, as described, thereby allowing the complex to form.

Kits are provided comprising the binding compound, as described, and: a compartment comprising the binding compound; and/or instructions for use or disposal of reagents in the kit. Other forms of the compositions include those comprising: a sterile binding compound, as described, or the binding compound and a carrier, wherein the carrier is: an aqueous compound, including water, saline, and/or buffer; and/or formulated for oral, rectal, nasal, topical, or parenteral administration. Typically, the kit comprises the described binding compound and: a compartment comprising that binding compound; and/or instructions for use or disposal of reagents in the kit. The kit may also be capable of making a qualitative or quantitative analysis.

Other compositions include: a sterile binding compound described above, or the binding compound and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding a protein or peptide or fusion protein, as described, wherein: the IL-1δ or IL-1ε is from a mammal; the nucleic acid: encodes an antigenic peptide sequence of SEQ ID NO: 2, 4, 6, 13, or 15; encodes a plurality of antigenic peptide sequences of SEQ ID NO: 2, 4, 6, 13, or 15; exhibits identity over at least 23 contiguous nucleotides to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a rodent; comprises a natural full length coding sequence; is a hybridization probe for a gene encoding said IL-1δ or IL-1ε; or is a primer, PCR product, or mutagenesis primer. The invention further embraces an isolated or recombinant nucleic acid encoding a protein or peptide or fusion protein, as described, wherein: the protein, peptide, or fusion protein is IL-1δ or IL-1ε from a rodent or IL-1ε from a primate; or the nucleic acid: encodes an antigenic peptide sequence of SEQ ID NO: 2 or SEQ ID NO: 6, 13, or 15; encodes a plurality of distinct antigenic peptide sequences of SEQ ID NO: 2, 6, 13, or 15; exhibits identity over at least 23 contiguous nucleotides to a natural cDNA encoding the segment; is an expression vector; further comprises an origin of replication; is from a natural source; comprises a detectable label; comprises synthetic nucleotide sequence; is less than 6 kb, preferably less than 3 kb; is from a rodent; comprises a natural full length coding sequence; is a hybridization probe for a gene encoding the IL-1δ or IL-1ε; or is a PCR primer, PCR product, or mutagenesis primer; encodes an IL-1δ or an IL-1ε protein; wherein the IL-1δ or IL-1ε protein specifically binds to polyclonal antibodies generated against an immunogen selected the polypeptide of SEQ ID NO: 2; or the polypeptide of SEQ ID NO: 6, 13, or 15.

Other embodiments include a cell transformed with the described nucleic acid. In various cases, the cell is: a prokaryotic cell; a eukaryotic cell; a bacterial cell; a yeast cell; an insect cell; a mammalian cell; a mouse cell; a primate cell; or a human cell.

Certain kits include the described nucleic acid and: a compartment comprising the nucleic acid; a compartment comprising an IL-1δ or IL-1ε protein or polypeptide; and/or instructions for use or disposal of reagents in the kit. Preferably the kit is capable of making a qualitative or quantitative analysis.

Alternatively, the invention provides a nucleic acid which: hybridizes under wash conditions of 3° C. and less than 2M salt to SEQ ID NO: 1; hybridizes under wash conditions of 30° C. and less than 2 M salt to SEQ ID NO: 1, 3, 5, 12 or 14; exhibits at least about 85% identity over a stretch of at least about 30 nucleotides to a rodent IL-1δ; or exhibits at least about 85% identity over a stretch of at least about 30 nucleotides to a rodent IL-1ε. Preferably, the nucleic acid described: will hybridize when wash conditions are at 45° C. and/or 500 mM salt; or exhibits identity at least 90% and/or over a stretch of at least 55 nucleotides. More preferably, the nucleic acid above will: hybridize at wash conditions of 55° C. and/or 150 mM salt; or exhibit an identity of at least 95% and/or over a stretch of at least 75 nucleotides.

The invention also provides methods of making or using these compositions or compounds. Such include a method of modulating physiology or development of a cell or tissue culture cells comprising contacting said cell or cells with an agonist or antagonist of a mammalian IL-1δ or IL-L1ε. Typically, the contacting is in combination with an agonist or antagonist of IL-1α, IL-1RA, IL-1β, IL-1γ, IL-2, and/or IL-12; the contacting is with an antagonist, including binding composition comprising an antibody binding site which specifically binds an IL-1δ or IL-1ε; or the modulating is regulation of IFN-γ production.

BRIEF DESCRIPTION OF THE DRAWINGS

FIGS. 2A and B describe polypeptide sequences in the IL-1 family of cytokines. The position numbers refer to alignment, and are not residue numbers from the individual sequences. Various sites for interaction with receptor are: SITE A includes residues corresponding to positions numbered 16–19, 25–27, 32, 34–41, and 44; SITE B includes residues corresponding to positions numbered 9–12, 14, 52–60, 115, 117–118, 122–123, 168, and 170; and SITE C includes residues corresponding to positions numbered 84–109. B conformations correspond to positions 11–17; 22–27; 30–34; 48–53; 65–71; 77–83; 88–93; 110–117; 122–128; 135–139; 145–150; and 168–172. The sequences can be found in the sequence listing, as indicated: hIL-1ε (SEQ ID NO:15); mIL-1ε (residues 4–160 of SEQ ID NO:6); mIL-1δ (residues 3–160 of SEQ ID NO:2); hIL-1RA (residues 31–177 of SEQ ID NO:7); hIL-1γ (residues 37–193 of SEQ ID NO:8); mIL-1y (residues 36–192 of SEQ ID NO:9); hIL-1β (residues 117–269 of SEQ ID NO:10); hIL-1α (residues 127–271 of SEQ ID NO:11)

DETAILED DESCRIPTION OF THE PREFERRED EMBODIMENTS

Outline

Figure 1A:
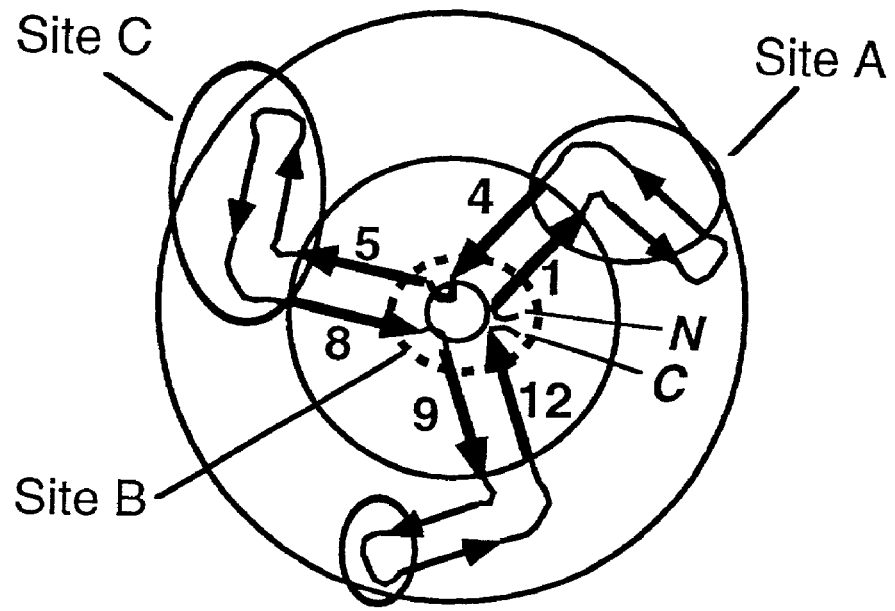
FIG. 1A is a cartoon depicting a top down view through the central axis of the predicted IL-1δ or IL-1ε protein demonstrating the characteristic tertiary β-trefoil structure with its 3-fold symmetric topology. Contact sites of the IL-1δ or IL-1ε protein that are predicted to bind the IL-1 receptor subunits are designated as sites A, B or C (FIG. 2). Contact sites A and C bind to the first receptor subunit of IL-1, while contact site B binds to the IL-1 second receptor subunit.
Figure 1B:
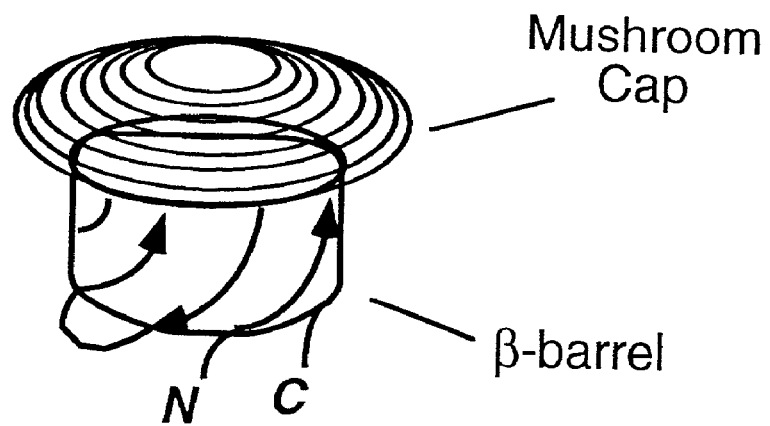
FIG. 1B is a cartoon depicting a side view of the predicted IL-1δ and IL-1ε protein demonstrating the barrel structure formed by the twelve β domains and a mushroom-like cap.

I. General
II. Activities
III. Nucleic Acids
   A. encoding fragments, sequence, probes
   B. mutations, chimeras, fusions
   C. making nucleic acids
   D. vectors, cells comprising
IV. Proteins, Peptides
   A. fragments, sequence, immunogens, antigens
   B. muteins
   C. agonists/antagonists, functional equivalents
   D. making proteins
V. Making nucleic acids, proteins
VI. Antibodies
   A. polyclonals
   B. monoclonal, Kd
   C. anti-idiotypic antibodies
   D. hybridoma cell lines
VII. Kits and Methods to quantify IL-1δ or IL-L1ε
   A. ELISA
   B. assay mRNA encoding
   C. qualitative/quantitative
   D. kits
VIII. Therapeutic compositions, methods
   A. combination compositions
   B. unit dose
   C. administration
IX. Receptors I. General Before the present compositions, formulations, and methods are described, it is to be understood that this invention is not limited to the particular methods, compositions, and cell lines described herein, as such methods, compositions, and cell lines may, of course, vary. It is also to be understood that the terminology used herein is for the purpose of describing particular embodiments only, and is not intended to limit the scope of the present invention which is only defined by the appended claims.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, all technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. All publications, patent applications, patents, and other references discussed above are provided solely for their disclosure prior to the filing date of the present application. Nothing herein is to be construed as an admission that the invention is not entitled to antedate any such disclosure by virtue of its prior invention. All publications, patent applications, patents, and other references mentioned herein are incorporated by reference in their entirety including all figures and drawings.

The present invention provides the amino acid sequence and DNA sequence of mammalian, e.g., rodent, interleukin-1 like molecules having particular defined properties, both structural and biological. These have been designated herein as interleukin-1δ (IL-1δ) and interleukin-1ε (IL-1ε), respectively, and increase the number of members of the IL-1 family from 4 to 6. Various cDNAs encoding these molecules were obtained from rodent, e.g., mouse, cDNA sequence libraries. Primate counterparts should also exist. The nucleic acids encompassed herein include DNA, cDNA, and RNA sequences which encode IL-1δ and IL-1ε. It is understood that nucleic acids encoding all or a portion of IL-1δ and IL-1ε polypeptides are also encompassed, so long as they encode a polypeptide with IL-1δ or IL-1ε activity. Such nucleic acids include both naturally occurring and intentionally manipulated nucleic acids. For example, IL-1δ or IL-1ε may be subjected to site-directed mutagenesis.

Some of the standard methods applicable are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and periodic supplements) *Current Protocols in Molecular Biology*, Greene/Wiley, New York; each of which is incorporated herein by reference.

A complete nucleotide (SEQ ID NO: 1) and corresponding amino acid sequence (SEQ ID NO: 2) of a rodent IL-1δ coding segment is shown in Table 1. A partial nucleotide (SEQ ID NO: 3) and corresponding amino acid sequence (SEQ ID NO: 4), as well as a full length nucleic acid (SEQ ID NO: 5) and corresponding amino acid sequence (SEQ ID NO: 6) of a rodent IL-1ε coding segment are shown in Table 2. Included also are primate, e.g., human sequences (SEQ ID NO: 12–15).

Table 4 shows relationship of IL-1 family members, and FIG. 2 provides an alignment of selected family members.

TABLE 1

Nucleotide and amino acid sequences (see SEQ ID NO: 1 and 2) of a mammalian, e.g., rodent, IL-1δ. The coding sequence does not indicate a signal sequence, which has been reported for various forms of messages encoding other members of the IL-1 family. Another form of the message probably encodes a signal sequence much like the IL-1β prodomain which is cleaved by a convertase-like enzyme, see Dinarello (1994) FASEBJ. 1314–1325).

```
ATG ATG GTT CTG AGT GGG GCA CTA TGC TTC CGA ATG AAG GAT TCA GCC        48
Met Met Val Leu Ser Gly Ala Leu Cys Phe Arg Met Lys Asp Ser Ala
 1               5                  10                  15

TTG AAG GTA CTG TAT CTG CAC AAT AAC CAG CTG CTG GCT GGA GGA CTG        96
Leu Lys Val Leu Tyr Leu His Asn Asn Gln Leu Leu Ala Gly Gly Leu
                20                  25                  30

CAC GCA GAG AAG GTC ATT AAA GGT GAG GAG ATC AGT GTT GTC CCA AAT       144
His Ala Glu Lys Val Ile Lys Gly Glu Glu Ile Ser Val Val Pro Asn
            35                  40                  45

CGG GCA CTG GAT GCC AGT CTG TCC CCT GTC ATC CTG GGC GTT CAA GGA       192
Arg Ala Leu Asp Ala Ser Leu Ser Pro Val Ile Leu Gly Val Gln Gly
        50                  55                  60

GGA AGC CAG TGC CTA TCT TGT GGG ACA GAG AAA GGG CCA ATT CTG AAA       240
Gly Ser Gln Cys Leu Ser Cys Gly Thr Glu Lys Gly Pro Ile Leu Lys
65                  70                  75                  80

CTT GAG CCA GTG AAC ATC ATG GAG CTC TAC CTC GGG GCC AAG GAA TCA       288
Leu Glu Pro Val Asn Ile Met Glu Leu Tyr Leu Gly Ala Lys Glu Ser
                85                  90                  95

AAG AGC TTC ACC TTC TAC CGG CGG GAT ATG GGT CTT ACC TCC AGC TTC       336
Lys Ser Phe Thr Phe Tyr Arg Arg Asp Met Gly Leu Thr Ser Ser Phe
                100                 105                 110

GAA TCC GCT GCC TAC CCA GGC TGG TTC CTC TGC ACC TCA CCG GAA GCT       384
Glu Ser Ala Ala Tyr Pro Gly Trp Phe Leu Cys Thr Ser Pro Glu Ala
                115                 120                 125

GAC CAG CCT GTC AGG CTC ACT CAG ATC CCT GAG GAC CCC GCC TGG GAT       432
Asp Gln Pro Val Arg Leu Thr Gln Ile Pro Glu Asp Pro Ala Trp Asp
            130                 135                 140

GCT CCC ATC ACA GAC TTC TAC TTT CAG CAG TGT GAC TA                    470
Ala Pro Ile Thr Asp Phe Tyr Phe Gln Gln Cys Asp
145                 150                 155
```

TABLE 2

Partial nucleotide and amino acid sequences (see SEQ ID NO: 3 and 4) of a mammalian, e.g., rodent, IL-1ε . . .

```
TTC CAG GAA GGG AAC ATA ATG GAA ATG TAC AAC AAA AAG GAA CCT GTA    48
Phe Gln Glu Gly Asn Ile Met Glu Met Tyr Asn Lys Lys Glu Pro Val
 1               5                  10                  15

AAA GCC TCT CTC TTC TAT CAC AAG AAG AGT GGT ACA ACC TCT ACA TTT    96
Lys Ala Ser Leu Phe Tyr His Lys Lys Ser Gly Thr Thr Ser Thr Phe
                20                  25                  30

GAG TCT GCA GCC TTC CCT GGT TGG TTC ATC GCT GTC TGC TCT AAA GGG   144
Glu Ser Ala Ala Phe Pro Gly Trp Phe Ile Ala Val Cys Ser Lys Gly
         35                  40                  45

AGC TGC CCA CTC ATT CTG ACC CAA GAA CTG GGG GAA ATC TTC ATC ACT   192
Ser Cys Pro Leu Ile Leu Thr Gln Glu Leu Gly Glu Ile Phe Ile Thr
     50                  55                  60

GAC TTC GAG ATG ATT GTG GTA CAT TAA    219
Asp Phe Glu Met Ile Val Val His
 65              70
```

. . . and complete mouse IL-1ε sequence (see SEQ ID NO: 5 and 6).

```
GAATTCGGCA CGAGTGTAGT GTGCAGACAC ATTCCTTATT CAATCAGGGT CAATCTGCAG    60

ATTGGCAGCT CAGGAACAAC ATCACCATA ATG AAT AAG GAG AAA GAA CTA AGA   113
                                Met Asn Lys Glu Lys Glu Leu Arg
                                 1               5

GCA GCA TCA CCT TCG CTT AGA CAT GTT CAG GAT CTT AGT AGT CGT GTG   161
Ala Ala Ser Pro Ser Leu Arg His Val Gln Asp Leu Ser Ser Arg Val
         10                  15                  20

TGG ATC CTG CAG AAC AAT ATC CTC ACT GCA GTC CCA AGG AAA GAG CAA   209
Trp Ile Leu Gln Asn Asn Ile Leu Thr Ala Val Pro Arg Lys Glu Gln
 25                  30                  35                  40

ACA GTT CCA GTC ACT ATT ACC TTG CTC CCA TGC CAA TAT CTG GAC ACT   257
Thr Val Pro Val Thr Ile Thr Leu Leu Pro Cys Gln Tyr Leu Asp Thr
                 45                  50                  55

CTT GAG ACG AAC AGG GGG GAT CCC ACG TAC ATG GGA GTG CAA AGG CCG   305
Leu Glu Thr Asn Arg Gly Asp Pro Thr Tyr Met Gly Val Gln Arg Pro
             60                  65                  70

ATG AGC TGC CTG TTC TGC ACA AAG GAT GGG GAG CAG CCT GTG CTA CAG   353
Met Ser Cys Leu Phe Cys Thr Lys Asp Gly Glu Gln Pro Val Leu Gln
         75                  80                  85

CTT GGG GAA GGG AAC ATA ATG GAA ATG TAC AAC AAA AAG GAA CCT GTA   401
Leu Gly Glu Gly Asn Ile Met Glu Met Tyr Asn Lys Lys Glu Pro Val
     90                  95                 100

AAA GCC TCT CTC TTC TAT CAC AAG AAG AGT GGT ACA ACC TCT ACA TTT   449
Lys Ala Ser Leu Phe Tyr His Lys Lys Ser Gly Thr Thr Ser Thr Phe
105                 110                 115                 120

GAG TCT GCA GCC TTC CCT GGT TGG TTC ATC GCT GTC TGC TCT AAA GGG   497
Glu Ser Ala Ala Phe Pro Gly Trp Phe Ile Ala Val Cys Ser Lys Gly
                125                 130                 135

AGC TGC CCA CTC ATT CTG ACC CAA GAA CTG GGG GAA ATC TTC ATC ACT   545
Ser Cys Pro Leu Ile Leu Thr Gln Glu Leu Gly Glu Ile Phe Ile Thr
            140                 145                 150

GAC TTC GAG ATG ATT GTG GTA CAT TAAGGTTTTT AGACACCTTG CTCTGTGGCA   599
Asp Phe Glu Met Ile Val Val His
            155                 160

CTCTCTCAAG ATTTCTTGGA TTCTAACAAG AAGCAATCAA AGACACCCCT AACAAAATGG   659

AAGACTGAAA AGAAAGCGA GCCCTCCCTG GCTGTTTTTT CCTTGGTGGT GAATCAGATG    719

CAGAACATCT TACCATGTTT TCATCCAAAG CATTTACTGT TGGTTTTTAC AAGGAGTGAA   779

TTTTTTAAAA TAAAATCATT TATCTCATAA    809
```

TABLE 2-continued

Partial primate, e.g., human, IL-1ε (see SEQ ID NO: 12 and 13);
nucleotide 144 designated G, may be G or T; nucleotide 451
designated C, may be C or T; and
nucleotide 469 designated C, may be A, C, G, or T:

| | |
|---|---|
| ATG AGA GGC ACT CCA GGA GAC GCT GAT GGT GGA GGA AGG GCC GTC TAT<br>Met Arg Gly Thr Pro Gly Asp Ala Asp Gly Gly Gly Arg Ala Val Tyr<br>1                      5                          10                      15 | 48 |
| CAA TCA ATG TGT AAA CCT ATT ACT GGG ACT ATT AAT GAT TTG AAT CAG<br>Gln Ser Met Cys Lys Pro Ile Thr Gly Thr Ile Asn Asp Leu Asn Gln<br>                  20                      25                      30 | 96 |
| CAA GTG TGG ACC CTT CAG GGT CAG AAC CTT GTG GCA GTT CCA CGA AGG<br>Gln Val Trp Thr Leu Gln Gly Gln Asn Leu Val Ala Val Pro Arg Arg<br>           35                      40                      45 | 144 |
| ACC AGT GTG ACC CCA GTC ACT GTT GCT GTT ATC ACA TGC AAG TAT CCA<br>Thr Ser Val Thr Pro Val Thr Val Ala Val Ile Thr Cys Lys Tyr Pro<br>50                      55                      60 | 192 |
| GAG GCT CTT GAG CAA GGC AGA GGG GAT CCC ATT TAT TTG GGA ATC CAG<br>Glu Ala Leu Glu Gln Gly Arg Gly Asp Pro Ile Tyr Leu Gly Ile Gln<br>65                      70                      75                      80 | 240 |
| AAT CCA GAA ATG TGT TTG TAT TGT GAG AAG GTT GGA GAA CAG CCC ACA<br>Asn Pro Glu Met Cys Leu Tyr Cys Glu Lys Val Gly Glu Gln Pro Thr<br>                  85                      90                      95 | 288 |
| TTG CAG CTA AAA GAG CAG AAG ATC ATG GAT CTG TAT GGC CAA CCC GAG<br>Leu Gln Leu Lys Glu Gln Lys Ile Met Asp Leu Tyr Gly Gln Pro Glu<br>           100                     105                     110 | 336 |
| CCC GTG AAA CCC TTC CTT TTC TAC CGT GCC AAG ACT GGT AGG AGG TCC<br>Pro Val Lys Pro Phe Leu Phe Tyr Arg Ala Lys Thr Gly Arg Arg Ser<br>           115                     120                     125 | 384 |
| ACC CTT GAG TCT GTG GCC TTC CCG GAC TGG TTC ATT GCC TCC TCC AAG<br>Thr Leu Glu Ser Val Ala Phe Pro Asp Trp Phe Ile Ala Her Ser Lys<br>130                     135                     140 | 432 |
| GGA GAC CAG CCC ATC ATT CTG ACT TCA GAA CTT TGG CAG TCA TAC AAC<br>Gly Asp Gln Pro Ile Ile Leu Thr Ser Glu Leu Trp Gln Ser Tyr Asn<br>145                     150                     155                     160 | 480 |
| ACT GCC TTT GAA TTA AAT ATT AAT G<br>Thr Ala Phe Glu Leu Asn Ile Asn<br>                  165 | 505 |

Supplemental primate, e.g., human, IL-1ε sequence
(see SEQ ID NO: 14 and 15) provides complete sequence.

| | |
|---|---|
| CCACGATTCA GTCCCCTGGA CTGTAGATAA AGACCCTTTC TTGCCAGGTG CTGAGACAAC | 60 |
| CACACT ATG AGA GGC ACT CCA GGA GAC GCT GAT GGT GGA GGA AGG GCC<br>        Met Arg Gly Thr Pro Gly Asp Ala Asp Gly Gly Gly Arg Ala<br>         1                      5                          10 | 108 |
| GTC TAT CAA TCA ATG TGT AAA CCT ATT ACT GGG ACT ATT AAT GAT TTG<br>Val Tyr Gln Ser Met Cys Lys Pro Ile Thr Gly Thr Ile Asn Asp Leu<br>15                      20                      25                      30 | 156 |
| AAT CAG CAA GTG TGG ACC CTT CAG GGT CAG AAC CTT GTG GCA GTT CCA<br>Asn Gln Gln Val Trp Thr Leu Gln Gly Gln Asn Leu Val Ala Val Pro<br>                  35                      40                      45 | 204 |
| CGA AGT GAC AGT GTG ACC CCA GTC ACT GTT GCT GTT ATC ACA TGC AAG<br>Arg Ser Asp Ser Val Thr Pro Val Thr Val Ala Val Ile Thr Cys Lys<br>                  50                      55                      60 | 252 |
| TAT CCA GAG GCT CTT GAG CAA GGC AGA GGG GAT CCC ATT TAT TTG GGA<br>Tyr Pro Glu Ala Leu Glu Gln Gly Arg Gly Asp Pro Ile Tyr Leu Gly<br>65                      70                      75 | 300 |
| ATC CAG AAT CCA GAA ATG TGT TTG TAT TGT GAG AAG GTT GGA GAA CAG<br>Ile Gln Asn Pro Glu Met Cys Leu Tyr Cys Glu Lys Val Gly Glu Gln<br>80                      85                      90 | 348 |
| CCC ACA TTG CAG CTA AAA GAG CAG AAG ATC ATG GAT CTG TAT GGC CAA | 396 |

TABLE 2-continued

```
Pro Thr Leu Gln Leu Lys Glu Gln Lys Ile Met Asp Leu Tyr Gly Gln
95                  100                 105                 110

CCC GAG CCC GTG AAA CCC TTC CTT TTC TAC CGT GCC AAG ACT GGT AGG    444
Pro Glu Pro Val Lys Pro Phe Leu Phe Tyr Arg Ala Lys Thr Gly Arg
                115                 120                 125

ACC TCC ACC CTT GAG TCT GTG GCC TTC CCG GAC TGG TTC ATT GCC TCC    492
Thr Ser Thr Leu Glu Ser Val Ala Phe Pro Asp Trp Phe Ile Ala Ser
                130                 135                 140

TCC AAG AGA GAC CAG CCC ATC ATT CTG ACT TCA GAA CTT GGG AAG TCA    540
Ser Lys Arg Asp Gln Pro Ile Ile Leu Thr Ser Glu Leu Gly Lys Ser
            145                 150                 155

TAC AAC ACT GCC TTT GAA TTA AAT ATA AAT GAC TGAACTCAGC CTAGAGGTGG  593
Tyr Asn Thr Ala Phe Glu Leu Asn Ile Asn Asp
160                 165

CAGCTTGGTC TTTGTCTTAA AGTTTCTGGT TCCCAATGTG TTTTCGTCTA CATTTTCTTA  653

GTGTCATTTT CACGCTGGTG CTGAGACAGG GGCAAGGCTG CTGTTATCAT CTCATTTTAT  713

AATGAAGAAG AAGCAATTAC TTCATAGCAA CTGAAGAACA GGATGTGGCC TCAGAAGCAG  773

GAGAGCTGGG TGGTATAAGG CTGTCCTCTC AAGCTGGTGC TGTGTAGGCC ACAAGGCATC  833

TGCATGAGTG ACTTTAAGAC TCAAAGACCA AACACTGAGC TTTCTTCTAG GGGTGCGTAT  893

GAAGATGCTT CAGAGCTCAT GCGCGTTACC CACGATGGCA TGACTAGCAC AGAGCTGATC  953

TCTGTTTCTG TTTTGCTTTA TTCCCTCTTG GGATGATATC ATCCAGTCTT TATATGTTGC  1013

CAATATACCT CATTGTGTGT AATAGAACCT TCTTAGCATT AAGACCTTGT AAACAAAAT   1073

AATTCTTGTG TTAAGTTAAA TCATTTTTGT CCTAATTGTA ATGTGTAATC TTAAAGTTAA  1133

ATAAACTTTG TGTATTTATA TAATAATAAA GCTAAAACTG ATATAAAAAA AAAAAAAAA   1193

AA                                                                  1195

MRGTPGDADGGGRAVYQSMCKPITGTINDLNQQVWTLQGQNLVAVPRSDSVTPVTVAVITCKYPEALEQ

GRGDPIYLGIQNPEMCLYCEKVGEQPTLQLKEQKIMDLYGQPEPVKPFLFYRAKTGRTSTLESVAFPDW

FIASSKRDQPIILTSELGKSYNTAFELNIND
```

TABLE 3

β conformation boundaries for IL-1δ (SEQ ID NO: 2) and IL-1ε (SEQ ID NO: 6). The presence of amino acid residues between β conformations β4 and β5 are characteristic of IL-1 agonists. IL-1 family molecules have highly conserved residues in the region encompassing β conformations β9 and β10.

| Cytokine | β conformation | Boundary |
|---|---|---|
| mouse IL-1δ | β1 | Leu8-Asp14 |
|  | β2 | Val19-Asn24 |
|  | β3 | Leu27-Gly31 |
|  | β4 | Ile43-Asn48 |
|  | β5 | Ser56-Val62 |
|  | β6 | Gln67-Thr73 |
|  | β7 | Pro77-Glu82 |
|  | β8 | Phe99-Met106 |
|  | β9 | Leu108-Ser114 |
|  | β10 | Phe121-Ser125 |
|  | β11 | Gln130-Thr135 |
|  | β12 | Gln153-Asp156 |
| mouse IL-1ε | β1 | Ser13-Asp19 |
|  | β2 | Val24-Asn29 |
|  | β3 | Ile31-Val35 |
|  | β4 | Ile46-Cys51 |
|  | β5 | Asp63-Val69 |
|  | β6 | Ser74-Lys80 |
|  | β7 | Pro85-Gly90 |
|  | β8 | Ser107-Ser114 |
|  | β9 | Thr116-Ser122 |
|  | β10 | Phe129-Cys133 |
|  | β11 | Cys138-Thr143 |
|  | β12 | Ile157-His160 |

TABLE 4

IL-1 FAMILY HOMOLOGY

```
                  ┌─── mIL-1g
              ┌───┤
              │   └─── hIL-1g
          ┌───┤
          │   │   ┌─── mIL-1e
          │   └───┤
      ┌───┤       └─── hIL-1e
      │   │       ┌─── mIL-1d
      │   └───────┤
      │           └─── hIL-1ra
      │
      │   ┌─────── hIL-1b
      └───┤
          └─────── hIL-1a 0.1
```

| % | hIL-1α | hIL-1β | hIL-1γ | mIL-1δ | mIL-1ε | hIL-1ra |
|---|--------|--------|--------|--------|--------|---------|
| hIL-1α |  | 22 | 13 | 16 | 20 | 17 |
| hIL-1β | 37 |  | 15 | 24 | 25 | 25 |
| hIL-1γ | 28 | 32 |  | 17 | 19 | 14 |
| mIL-1δ | 36 | 38 | 31 |  | 37 | 42 |
| mIL-1ε | 37 | 40 | 38 | 48 |  | 23 |
| hIL-1ra | 38 | 46 | 32 | 54 | 45 |  |

% Protein Identity (upper right) / % DNA Identity (lower left)

As used herein, the term IL-1δ shall be used to describe a protein comprising a protein or peptide segment having or sharing the amino acid sequence shown in Table 1, or a substantial fragment thereof. Similarly, with an IL-1ε and Table 2. The invention also includes protein variations of the IL-1δ allele whose sequence is provided, e.g., a mutein agonist or antagonist. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic variants, of the protein described. "Natural" as used herein means unmodified by artifice. Typically, it will bind to its corresponding biological receptor with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the mammalian protein.

This invention also encompasses proteins or peptides having substantial amino acid sequence homology with the amino acid sequence in Table 1 or 2. It will include sequence variants with relatively few substitutions, e.g., preferably less than about 3–5. Similar features apply to the IL-1ε sequence provided in Table 2.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches. Preferred embodiments exhibit a plurality of distinct, e.g., non-overlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

Amino acid sequence homology, or sequence identity, is determined by optimizing residue matches, if necessary, by introducing gaps as required. See, e.g., Needleham, et al., (1970) *J. Mol. Biol.* 48:443–453; Sankoff, et al., (1983) chapter one in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50–100% homology (if gaps can be introduced), to 60–100% homology (if conservative substitutions are included) with an amino acid sequence segments of Tables 1 or 2. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments described in Tables 1 and/or 2. As used herein, the term "biological activity" is used to describe, without limitation, effects on inflammatory responses and/or innate immunity. For example, they may, like IL-1γ, exhibit synergistic induction by splenocytes of IFN-γ in combination with IL-12 or IL-2, with or without anti-type I or anti-type II IL-1 receptor antibodies, or more structural properties as receptor binding and cross-reactivity with antibodies raised against the same or a polymorphic variant of a mammalian IL-1δ or IL-1ε.

For sequence comparison, typically one sequence acts as a reference sequence, to which test sequences are compared. When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351–360. The method used is similar to the method described by Higgins and Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403–410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below. Hybridization under stringent conditions should give a background of at least 2-fold over background, preferably at least 3–5 or more.

The terms ligand, agonist, antagonist, and analog of, e.g., IL-1δ, include molecules that modulate the characteristic cellular responses to IL-1δ or IL-1δ-like proteins, as well as molecules possessing the more standard structural binding competition features of ligand-receptor interactions, e.g., where the receptor is a natural receptor or an antibody. The cellular responses likely are mediated through binding of IL-1δ or IL-1ε to cellular receptors related to, but possibly distinct from, the type I or type II IL-1 receptors. Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds.) (1990) *Goodman & Gilman's: The Pharmacological Bases of Therapeutics*, Pergamon Press, New York.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York, which is hereby incorporated herein by reference.

II. Activities

The IL-1δ or IL-1ε proteins will have a number of different biological activities, e.g., in the immune system, and will include inflammatory functions or other innate immunity responses. The IL-1δ or IL-1ε proteins are homologous to other IL-1 proteins, but each have structural differences. For example, a human IL-1γ gene coding sequence probably has about 70% identity with the nucleotide coding sequence of mouse IL-1γ, and similar measures of similarity will apply to the IL-1δ and IL-1ε. At the amino acid level, there is also likely to be about 60% identity. This level of similarity suggests that the new IL-1δ and IL-1ε proteins are related to the other IL-1α and IL-1β and IL-1RA.

The mouse IL-1γ molecule has the ability to stimulate IFN-γ production which augments NK activity in spleen cells. See Okamura, et al. (1995) *Nature* 378:88–91.

The activities of the mouse IL-1α, IL-1β, and IL-1γ have been compared as to their ability to induce IFN-γ, alone or in combination with IL-2 or IL-12 in SCD splenocytes and purified NK cells. See Hunter, et al. (1995) *J. Immunol.* 155:4347–4354; and Bancroft, et al. (1991) *Immunol. Revs.* 124:5–24 [xxx]. The IL-1γ was found to be much more potent in stimulating IFN-1γ than either IL-1α or IL-1β. IL-1δ and IL-1ε and their agonists or antagonists should have related activities, typically affecting similar immune functions, including inflammatory responses.

In IL-2 activated NK cells, IFN-γ production is blocked by the addition of anti-IL-1β antibodies. See Hunter, et al. (1995). However, mouse IL-1γ can overcome this block and induce IFN-γ. This is the only cytokine known to be able to do this. In addition, in vivo, administration of mouse IL-1γ to mice infected with the parasite T. Cruzi significantly decreases parasitemia. IL-1δ and IL-1ε and their agonists or antagonists should operate through related mechanisms and effectors.

The present disclosure also describes new assays for activities predicted for the mouse IL-1δ or IL-1ε molecules. Corresponding activities should be found in other mammalian systems, including primates. It is likely that the new mouse IL-1-like molecules produced by similar recombinant means to the human IL-1γ protein should exhibit a biological activity of modulating lymphocyte cells in production of IFN-γ. See assays described, e.g., in de Waal Malefyt, et al., in de Vries and de Waal Malefyt (eds. 1995) "Interleukin-10" Landes Co., Austin, Tex. Furthermore, there is substantial likelihood of synergy with other IL-1 or IL-12 related agonists or antagonists. It is likely that the receptors, which are expected to include multiple different polypeptide chains, exhibit species specificity for their corresponding ligands. The IL-1α and IL-1β ligands both signal through heterodimeric receptors.

III. Nucleic Acids

This invention contemplates use of isolated nucleic acid or fragments, e.g., which encode this or a closely related protein, or fragments thereof, e.g., to encode a biologically active corresponding polypeptide. The term "isolated nucleic acid or fragments" as used herein means a nucleic acid, e.g., a DNA or RNA molecule, that is not immediately contiguous when present in the naturally occurring genome of the organism from which it is derived. Thus, the term describes, e.g., a nucleic acid that is incorporated into a vector, such as a plasmid or viral vector; a nucleic acid that is incorporated into the genome of a heterologous cell (or the genome of homologous cell, but at a site different from that at which it normally occurs); and a nucleic acid that exists as a separate molecule, e.g., a DNA fragment produced by PCR amplification or restriction enzyme digestion, or an RNA molecule produced by in vitro transcription. The term also describes a recombinant (i.e., genetically engineered) nucleic acid that forms part of a hybrid gene encoding additional polypeptide sequences that can be used, e.g., in the production of a fusion protein. In addition, this invention embodies any engineered or nucleic acid molecule created by artifice that encodes a biologically active protein or polypeptide having characteristic IL-1δ or IL-1ε activity.

Typically, the nucleic acid is capable of hybridizing, under appropriate conditions, with a nucleic acid sequence segment shown in Table 1 or 2. Said biologically active protein or polypeptide can be a full length protein, or fragment, and will typically have a segment of amino acid sequence highly homologous to one shown in Table 1 or 2. Further, this invention covers the use of isolated or recombinant nucleic acid, or fragments thereof, which encode proteins having fragments which are homologous to the newly disclosed IL-1-like proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, e.g., products made by transforming cells with any unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode similar polypeptides to fragments of the IL-1δ or IL-1ε and fusions of sequences from various different interleukin or related molecules, e.g., growth factors.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides including, e.g., 100, 150, 200, 250, etc. Typically, fragments of different genetic sequences can be compared to one another over appropriate length stretches, particularly defined segments such as the domains described below.

A nucleic acid which codes for an IL-1δ or IL-1ε will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous nucleic acid sequences, when compared to one another or Table 1 or 2 sequences, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from Table 1 or 2. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nuc. Acids Res.* 12:203–213. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. However, the combination of parameters is much more important than the measure of any single parameter. See, e.g., Wetmur and Davidson (1968) *J. Mol. Biol.* 31:349–370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant IL-1-like derivatives include predetermined or site-specific mutations of the protein or its fragments, including silent mutations using genetic code degeneracy. "Mutant IL-1δ" as used herein encompasses a polypeptide otherwise falling within the homology definition of the IL-1δ as set forth above, but having an amino acid sequence which differs from that of other IL-1-like proteins as found in nature, whether by way of deletion, substitution, or insertion. In particular, "site specific mutant IL-1δ" encompasses a protein having substantial homology with a protein of Table 1, and typically shares most of the biological activities of the form disclosed herein.

Although site specific mutation sites are predetermined, mutants need not be site specific. Mammalian IL-1δ mutagenesis can be achieved by making amino acid insertions or deletions in the gene, coupled with expression. Substitutions, deletions, insertions, or any combinations may be generated to arrive at a final construct. Insertions include amino- or carboxy-terminal fusions. Random mutagenesis can be conducted at a target codon and the expressed mammalian IL-1δ mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (1995; eds.) *PCR Primer: A Laboratory Manual* Cold Spring Harbor Press, CSH, N.Y.

IV. Proteins, Peptides

As described above, the present invention encompasses mammalian IL-1δ or IL-1ε, e.g., whose sequences are disclosed in Tables 1 or 2, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these rodent proteins. A heterologous fusion protein is a fusion of proteins or segments which are naturally not normally fused in the same manner. Thus, the fusion product of a growth factor with an interleukin is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional or structural domains from other related proteins, e.g., growth factors or other cytokines. For example, receptor-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of receptor-binding specificities. For example, the receptor binding domains from other related ligand molecules may be added or substituted for other domains of this or related proteins. The resulting protein will often have hybrid function and properties. For example, a fusion protein may include a targeting domain which may serve to provide sequestering of the fusion protein to a particular organ, e.g., a ligand portions which is specifically bound by spleen cells and would serve to accumulate in the spleen.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

The present invention particularly provides muteins which act as agonists or antagonists of the IL-1δ or IL-1ε. Structural alignment of mouse IL-1δ and mouse IL-1ε with other members of the IL-1 family show conserved features/ residues, particularly 12 β strands folded into a β-trefoil fold (see FIG. 1A; Table 3 and FIGS. 2A,B). The 12 mouse IL-1δβ strand domains are recited respectively (Table 3) as Leu8-Asp14, Val19-Asn24, Leu27-Gly31, Ile43-Asn48, Ser56-Val62, Gln67-Thr73, Pro77-Glu82, Phe99-Met106, Leu 108-Ser114, Phe121-Ser125, Gln130-Thn135, and Gln153-Asp156 of SEQ ID NO: 2; while the 12 mouse IL-1ε β strand domains are recited respectively (Table 3) as Ser13-Asp19, Val24-Asn29, Ile31-Val35, Ile46-Cys51, Asp63-Val69, Ser74-Lys80, Pro85-Gly90, Sen107-Ser114, Thr116-Sen122, Phe129-Cys133, Cys138-Thr143, and Ile157-His160 of SEQ ID NO: 6).

Alignment of the mouse IL-1δ and IL-1ε sequences (using the Met initiation residue as the first amino acid) with other members of the IL-1 family indicates that the β conformations correspond to similar sequences in other IL-1 family members (see Tables 3, 4, and FIGS. 2A,B). See also, Bazan, et al. (1996) *Nature* 379:591; Lodi, et al. (1994) *Science* 263:1762–1766; Sayle and Milner-White (1995) *TIBS* 20:374–376; and Gronenbeng, et al. (1991) *Protein Engineering* 4:263–269.

The IL-1α and IL-1β ligands bind an IL-1 receptor type I as the primary receptor and this complex then forms a high affinity receptor complex with the IL-1 receptor type III. Such receptor subunits are probably shared with the new IL-1 family members.

The mouse IL-1γ does not bind to the known mouse IL-1 receptor types I, II (decoy receptor), or III. In addition, the mouse IGIF biological activity cannot be blocked with anti-type I, II, or III antibodies. This suggests that the related mouse IGIF binds to receptors related to the IL-1 receptors already isolated, but not yet identified as receptors for the IGIF.

The solved structures for IL-1β, the natural IL-1 receptor antagonist (IL-1Ra), and a co-structure of IL-1Ra/IL-1 receptor type I, however, suggest how to make a mouse IL-1δ or IL-1ε antagonist (See, e.g., accession numbers: U65590, gbU19844, gbU19845, gi2173679, gi2170133, gi2172939, gbM15300, gbM28983, gbU65590, gbM74294, embX04964, gi2169698, gi2169368 emb270047, gi914939, gi220782, embX52731, embX56972 and embX12497, for various species examples of IL-1 family members). Structural analyses of the mature rodent IL-1δ or IL-1ε suggest that its β-trefoil structures contact the IL-1 receptor over three binding sites (designated A, B and C; FIG. 1A). Sites A and C bind to the first receptor subunit (alpha) of IL-1 while site B binds the IL-1 second receptor subunit (beta). Homology sequence comparison of the IL-1 family members reveals that the only known antagonist to IL-1 receptor (IL-1ra; Table 5) is missing an amino acid domain bounded by the β4 and β5 strands. This domain maps to a portion of site B in rodent IL-1δ or IL-1ε (Table 5) that binds to the IL-1 second receptor subunit, suggesting that its absence confers antagonist activity as evidenced by homology comparison among other IL-1 family members. This loop portion of contact site B spans approximately 7–10 amino residues, while in IL-1RA the loop is "cut off" with only 2 residues remaining. Therefore, IL-1RA binds normally to receptor type I, but cannot interact with receptor type III. This makes IL-1RA into an effective IL-1 antagonist.

The corresponding location in rodent IL-1δ or IL-1ε (between β4 and β5) defines a domain that forms a polypeptide loop which is part of a primary binding segment to the IL-1 receptor type (site B in FIGS. 2A,B). The loop, depicted pictorially in FIG. 1A as protruding into the central axis of the mature IL-1δ or IL-1ε protein, is located between arrows 4 and 5). More precisely, the loop is defined for IL-1δ by amino residues Pro47-Ala53 of SEQ ID NO: 2 and for IL-1ε by amino residues Pro50-Glu58 of SEQ ID NO: 6. Accordingly, IL-1δ or IL-1ε antagonist activity should be generated by removal all or an appropriate portion of a corresponding portion of amino acids located between β4 and β5. This suggests that analogous modifications to the loop between the β4 and the β5 strands will lead to variants with predictable biological activities. With mouse IL-1RA, it was shown that replacement of the mouse IL-1RA residues with those mouse IL-1β residues introduced IL-1 activity to the IL-1RA variant (IL-1RA could then bind type III receptor). Similar substitutions will establish that type III receptor can probably be used by mouse IL-1δ or IL-1ε proteins or muteins. Additional site B contacts are defined in rodent IL-1δ by amino residues 8–11, 13, 112, 114–117, 158 and 160 of SEQ ID NO: 2. Corresponding additional site B contacts are defined in mouse IL-1ε by amino residues 3–6, 8, 104, 106–109, 154 and 156 of SEQ ID NO: 6. Corresponding residues should be important in the primate sequence (see SEQ ID NO: 13 and 15).

Sites A and C (see FIGS. 2A,B) mediate binding of IL-1δ or IL-1ε to the first IL-1 receptor subunit, e.g., an alpha receptor subunit. Site A contacts correspond in IL-1δ to amino residues 13–16, 22–24, 29, 31–37, 39, 126–131, 151, and 153 of SEQ ID NO: 2; while site C contacts correspond in IL-1δ to amino residues 74–98 of SEQ ID NO: 2. Site A contacts are defined in IL-1ε by amino residues 18–21, 21–29, 33, 35–42, 134–139, 155, and 157 of SEQ ID NO: 6; while site C contacts correspond in IL-1ε to amino residues 81–106 of SEQ ID NO: 6. Corresponding residues should be important in the primate sequence (see SEQ ID NO: 13 and 15).

Similar variations in other species counterparts of IL-1δ or IL-1ε ligand sequence, e.g., in the corresponding regions, should provide similar interactions with receptor. Substitutions with either mouse sequences or human sequences are indicated. Conversely, conservative substitutions away from the receptor binding interaction regions will probably preserve most biological activities.

"Derivatives" of the mammalian IL-1δ include amino acid sequence mutants, glycosylation variants, metabolic derivatives and covalent or aggregative conjugates with other chemical moieties. Covalent derivatives can be prepared by linkage of functionality's to groups which are found in the IL-1δ amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the interleukin or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the interleukin and other homologous or heterologous proteins are also provided. Homologous polypeptides may be fusions between different growth factors, resulting in, for instance, a hybrid protein exhibiting ligand specificity for multiple different receptors, or a ligand which may have broadened or weakened specificity of binding to its receptor. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), Vols. 1–3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference. See also Dawson, et al. (1994) *Science* 266: 776–779 for methods to make larger polypeptides.

In another embodiment, the present invention relates to substantially purified peptide fragments of IL-1δ or IL-1ϵ that block binding between IL-1 family members and a target receptor. Such peptide fragments could represent research and diagnostic tools in the study of inflammatory reactions to antigenic challenge and the development of more effective anti-inflammatory therapeutics. In addition, pharmaceutical compositions comprising isolated and purified peptide fragments of IL-1δ or IL-1ϵ may represent effective anti-inflammatory therapeutics.

The term "substantially purified" as used herein refers to a molecule, such as a peptide that is substantially free of other proteins, lipids, carbohydrates, nucleic acids, or other biological materials with which it is naturally associated. For example, a substantially pure molecule, such as a polypeptide, can be at least 60%, by dry weight, the molecule of interest. One skilled in the art can purify IL-1δ or IL-1ϵ peptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The invention relates not only to fragments of naturally-occurring IL-1δ or IL-1ϵ, but also to IL-1δ or IL-1ϵ mutants and chemically synthesized derivatives of IL-1δ or IL-1ε that block binding between IL-1 family members and a target receptor.

For example, changes in the amino acid sequence of IL-1δ or IL-1ε are contemplated in the present invention. IL-1δ or IL-1ε can be altered by changing the nucleic acid sequence encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of IL-1δ or IL-1ε can be used in the present invention. Variants include analogs, homologues, derivatives, muteins, and mimetics of IL-1δ or IL-1ε that retain the ability to block binding between IL-1 family members and a target receptor. Fragments of the IL-1δ or IL-1ε refer to portions of the amino acid sequence of IL-1δ or IL-1ε as defined in SEQ ID NO: 2, 4, 6, 13, or 15 that also retain this ability. The variants and fragments can be generated directly from IL-1δ or IL-1ε itself by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of IL-1δ or IL-1ε ("mimetics") can be produced by the approach outlined in Saragovi, et al. (1991) *Science* 253: 792–95. Mimetics are molecules which mimic elements of protein secondary structure. See, e.g., Johnson et al. "Peptide Turn Mimetics" in Pezzuto, et al. (eds. 1993) *Biotechnology and Pharmacy*, Chapman and Hall, New York. The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of IL-1δ or IL-1ε itself.

Variants and fragments also can be created by recombinant techniques employing genomic or cDNA cloning methods. Site-specific and region-directed mutagenesis techniques can be employed. See, e.g., vol. 1, ch. 8 in Ausubel, et al. (eds. 1989 and periodic updates) *Current Protocols in Molecular Biology* Wiley and Sons; and Oxender and Fox (eds.) *Protein Engineering* Liss, Inc. In addition, linker-scanning and PCR-mediated techniques can be employed for mutagenesis. See, e.g., Erlich (ed. 1989) *PCR Technology* Stockton Press. Protein sequencing, structure and modeling approaches for use with any of the above techniques are disclosed, e.g., in Oxender and Fox (eds.) *Protein Engineering* Liss, Inc.; and Ausubel, et al. (eds. 1989 and periodic updates) *Current Protocols in Molecular Biology* Wiley and Sons.

This invention also contemplates the use of derivatives of IL-1δ other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, e.g., with cell membranes. Such covalent or aggregative derivatives are useful as immunogens, as reagents in immunoassays, or in purification methods such as for affinity purification of a receptor or other binding molecule, e.g., an antibody. For example, an IL-1δ ligand can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of IL-1δ receptor, antibodies, or other similar molecules. The IL-1δ can also be labeled with a detectable group, e.g., radio-iodinated by the chloramine T procedure, covalently bound to rare earth chelates, or conjugated to another fluorescent moiety for use in diagnostic assays.

An IL-1δ of this invention can be used as an immunogen for the production of antisera or antibodies specific, e.g., capable of distinguishing between other IL-1 family members and an IL-1δ, for the interleukin or any fragments thereof. The purified interleukin can be used to screen monoclonal antibodies or antigen-binding fragments prepared by immunization with various forms of impure preparations containing the protein. In particular, the term "antibodies" also encompasses antigen binding fragments of natural antibodies. The purified interleukin can also be used as a reagent to detect any antibodies generated in response to the presence of elevated levels of expression, or immunological disorders which lead to antibody production to the endogenous cytokine. Additionally, IL-1δ fragments may also serve as immunogens to produce the antibodies of the present invention, as described immediately below. For example, this invention contemplates antibodies having binding affinity to or being raised against the amino acid sequence shown in Table 1, fragments thereof, or homologous peptides. In particular, this invention contemplates antibodies having binding affinity to, or having been raised against, specific fragments which are predicted to be, or actually are, exposed at the exterior protein surface of the native cytokine.

The blocking of physiological response to these interleukins may result from the inhibition of binding of the ligand to the receptor, likely through competitive inhibition. Thus, in vitro assays of the present invention will often use antibodies or ligand binding segments of these antibodies, or fragments attached to solid phase substrates. These assays will also allow for the diagnostic determination of the effects of either binding region mutations and modifications, or ligand mutations and modifications, e.g., ligand analogs.

This invention also contemplates the use of competitive drug screening assays, e.g., where neutralizing antibodies to the interleukin or fragments compete with a test compound for binding to a receptor or antibody. In this manner, the neutralizing antibodies or fragments can be used to detect the presence of any polypeptide which shares one or more binding sites to a receptor and can also be used to occupy binding sites on a receptor that might otherwise bind an interleukin.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Table 1. Other species counterparts can be identified by hybridization techniques, or by various PCR techniques, combined with or by searching in sequence databases.

This DNA can be expressed in a wide variety of host cells for the synthesis of a full-length interleukin or fragments which can in turn, e.g., be used to generate polyclonal or monoclonal antibodies; for binding studies; for construction and expression of modified agonist/antagonist molecules; and for structure/function studies. Each variant or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or dilutent. The protein, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the interleukin protein or its fragments in various hosts using vectors that do not contain a replication origin that is recognized by the host cell. It is also possible to use vectors that cause integration of the protein encoding portion or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds.) *Vectors: A Survey of Molecular Cloning Vectors and Their Uses*, Buttersworth, Boston, 1988, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the interleukin to accumulate in the culture. The protein can be recovered, either from the culture or from the culture medium.

For purposes of this invention, nucleic sequences are operably linked when they are functionally related to each other. For example, DNA for a pre-sequence or secretory leader is operably linked to a polypeptide if it is expressed as a pre-protein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses*, (eds. Rodriguez and Denhardt), Buttersworth, Boston, Chapter 10, pp. 205–236, which is incorporated herein by reference.

Lower eukaryotes, e.g., yeasts and Dictyostelium, may be transformed with IL-1γ sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo PolyA, see Thomas, et al. (1987) *Cell* 51:503–512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683–4690, and the precise amino acid composition of the signal peptide does not appear to be critical to its function, e.g., Randall, et al. (1989) *Science* 243:1156–1159; Kaiser et al. (1987) *Science* 235:312–317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the interleukin gene may be co-transformed with one or more genes encoding mammalian or other glycosylating enzymes. Using this approach, certain mammalian glycosylation patterns will be achievable in prokaryote or other cells.

The source of IL-1δ or IL-1ε can be a eukaryotic or prokaryotic host expressing recombinant IL-1δ or IL-1ε DNA, such as is described above. The source can also be a cell line such as mouse Swiss 3T3 fibroblasts, but other mammalian cell lines are also contemplated by this invention, with the preferred cell line being from the human species.

Now that the entire sequence is known, the rodent IL-1δ, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes. Similar techniques can be used with the partial IL-1ε sequence.

The IL-1δ protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble-carrier to produce the peptide. This solid-phase approach is generally described by Merrifield, et al. (1963) in *J. Am. Chem. Soc.* 85:2149–2156, which is incorporated herein by reference.

The prepared protein and fragments thereof can be isolated and purified from the reaction mixture by means of peptide separation, e.g., by extraction, precipitation, electrophoresis, various forms of chromatography, and the like. The interleukin of this invention can be obtained in varying degrees of purity depending upon its desired use. Purification can be accomplished by use of the protein purification techniques disclosed herein, see below, or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the interleukin, or lysates or supernatants of cells producing the protein as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%-99% or more. Purity will usually be on a weight basis, but can also be on a molar basis. Different assays will be applied as appropriate.

VI. Antibodies

The term "antibody" or "antibody molecule" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (4) Fv, defined as a genetically engineered fragment containing the variable region of the light chain and the variable region of the heavy chain expressed as two chains; and (5) single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, e.g., Harlow and Lane (current edition) *Antibodies: A Laboratory Manual*, Cold Spring Harbor Laboratory, New York. Therefore, the phrase "antibody molecule" in its various forms as used herein contemplates both an intact antibody (immunoglobulin) molecule and an immunologically active portion of an antibody (immunoglobulin) molecule. Recombinant methods may be applied to make these fragments.

The term "monoclonal antibody" refers to a population of one species of antibody molecule of antigen-specificity. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen. In one embodiment, the first antibody molecule is affixed to a solid support. In addition, the antibody molecules in a phage display combinatorial library are also monoclonal antibodies.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The word "complex" as used herein refers to the product of a specific binding agent-ligand reaction. An exemplary complex is an immunoreaction product formed by an antibody-antigen reaction.

The term "antigen" refers to a polypeptide or protein that is able to specifically bind to (immunoreact with) an antibody and form an immunoreaction product (immunocomplex). The site on the antigen with which the antibody binds is referred to as an antigenic determinant or epitope, and the labeling should be detectable, e.g., 2×, 5× or more above background.

The method of the invention for detection of antibodies that bind to novel epitopes in a sample is performed in vitro, e.g., in immunoassays in which the antibodies can be identified in liquid phase or bound to a solid phase carrier. Preferably, the method is performed with a capture antibody bound to a solid support. Preferably, the capture antibody is a monoclonal antibody molecule.

Examples of types of immunoassays which can be utilized to detect novel antibodies in a sample, include competitive and non-competitive immunoassays in either a direct or indirect format. Examples of such immunoassays are the radioimmunoassay (RIA) and the sandwich (immunometric) assay. Detection of the antibodies can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules are bound by adsorption from an aqueous medium, although other modes of affixation, such as covalent coupling or other well known means of affixation to the solid matrix can be used. Preferably, the first antibody molecule is bound to a support before forming an immunocomplex with antigen, however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody-containing solid support at protein binding sites on the surface that are not occupied by the antibody molecule.

A typical aqueous protein solution contains about 2–10 weight percent bovine serum albumin in PBS at a pH of about 7–8. The aqueous protein solution-solid support mixture is typically maintained for a time period of at least one hour at a temperature of about 4°–37° C. and the resulting solid phase is thereafter rinsed free of unbound protein.

The first preselected antibody can be bound to many different carriers and used to detect novel epitope binding antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation.

In addition, if desirable, an antibody for detection in these immunoassays can be detectably labeled in various ways. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the antibodies used in the method of the invention can be done using standard techniques common to those of ordinary skill in the art.

Antibodies which bind to IL-1δ or IL-1ε polypeptides of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, e.g., by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies See, e.g., Coligan, et al. (current ed.) Unit 9, *Current Protocols in Immunology*, Wiley Interscience.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The preparation of polyclonal antibodies is well-known to those skilled in the art. See, e.g., Green, et al. "Production of Polyclonal Antisera" pages 1–5 in Manson (ed.) *Immunochemical Protocols* Humana Press; *Production of Polyclonal Antisera in Rabbits, Rats, Mice and Hamsters* section 2.4.1 in Coligan, et al. *Current Protocols in Immunology*.

The preparation of monoclonal antibodies likewise is conventional. See, e.g., Kohler and Milstein, *Nature* 256: 495 (1975); Coligan et al., sections 2.5.1–2.6.7; and Harlow et al., *Antibodies: A Laboratory Manual*, Cold Spring Harbor Press. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See. e.g., Coligan, et al., sections 2.7.1–2.7.12 and sections 2.9.1–2.9.3; Barnes, et al. "Purification of Immunoglobulin G (IgG)" in *Methods in Molecular Biology*, vol. 10, pages 79–104 (Humana Press, current ed.). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished, e.g., by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngenic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications are conceivable for the antibodies of the present invention. For example, antibodies of the present invention may also be derived from subhuman primate antibody. General techniques for raising therapeutically useful antibodies in baboons may be found, e.g., in Goldenberg, et al. (1991) WO 91/11465; and Losman, et al. (1990) *Int. J. Cancer* 46:310.

Alternatively, a therapeutically useful anti-IL-1δ or anti-IL-1ε antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, e.g., by Orlandi, et al. (1989) *Proc. Nat'l Acad. Sci. USA* 86:3833. Techniques for producing humanized monoclonal antibodies are described, e.g., by Jones et al. (1986) *Nature* 321:522; Riechmann, et al. (1988) *Nature* 332:323; Verhoeyen, et al. (1988) *Science* 239:1534; Carter, et al. (1992) *Proc. Nat'l Acad. Sci. USA* 89:4285; Sandhu (1992) *Crit. Rev. Biotech.* 12:437; and Singer, et al. (1993) *J. Immunol.* 150:2844.

Antibodies of the invention also may be derived from human antibody fragments isolated from a combinatorial immunoglobulin library. See, e.g., Barbas, et al. (1991) *Methods: A Companion to Methods in Enzymology*, vol. 2, page 119; and Winter, et al. (1994) *Ann. Rev. Immunol.* 12:433. Cloning and expression vectors that are useful for producing a human immunoglobulin phage library can be obtained, e.g., from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green, et al. (1994) *Nature Genet.* 7:13; Lonberg, et al. (1994) *Nature* 368:856; and Taylor, et al. (1994) *Int. Immunol.* 6:579.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5 S Fab' monovalent fragments. Alternatively, an enzymatic cleavage using papain produces two monovalent Fab fragments and an Fc fragment directly. These methods are described, e.g., by Goldenberg, U.S. Pat. No. 4,036,945 and No. 4,331,647, and references contained therein. These patents are hereby incorporated in their entireties by reference including all figures, drawings, and illustrations. See also Nisonhoff, et al. (1960) *Arch. Biochem. Biophys.* 89:230; Porter (1959) *Biochem. J.* 73:119; Edelman, et al. (1967) *Methods in Enzymology*, vol. 1, Academic Press; and Coligan, et al., at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar, et al. (1972) *Proc. Nat'l Acad. Sci. USA* 69:2659. Alternatively, the variable chains can be linked by an intermolecular disulfide bond or cross-linked by chemicals such as glutaraldehyde. See, e.g., Sandhu (1992) *Crit. Rev. Biotech.* 12:437. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, e.g., by Whitlow, et al. (1991) *Methods: a Companion to Methods in Enzymology*, vol. 2, page 97; Bird, et al. (1988) *Science* 242:423–426; Ladner, et al., U.S. Pat. No. 4,946,778; Pack, et al. (1993) *Bio/Technology* 11:1271–77; and Sandhu (1992) *Crit. Rev. Biotech.* 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, e.g., by using the polymerase chain reaction to synthesize the variable region from RNA of antibody-producing cells. See, e.g., Larrick, et al. (1991) *Methods: A Companion to Methods in Enzymology*, vol. 2, page 106.

Antibodies can be raised to the various mammalian, e.g., rodent IL-1δ and/or IL-1ε proteins and fragments thereof, both in naturally occurring native forms and in their recombinant forms, the difference being that antibodies to the active ligand are more likely to recognize epitopes which are only present in the native conformations. Denatured antigen detection can also be useful in, e.g., Western analysis. Anti-idiotypic antibodies are also contemplated, which would be useful as agonists or antagonists of a natural receptor or an antibody.

A number of immunogens may be used to produce antibodies specifically reactive with thymokine proteins. Recombinant protein is the preferred immunogen for the production of monoclonal or polyclonal antibodies. Naturally occurring protein may also be used either in pure or impure form. Synthetic peptides made using the human or mouse lymphotactin protein sequences described herein may also used as an immunogen for the production of antibodies to thymokines. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the thymokine protein of interest. When appropriately high titers of antibody to the immunogen are obtained, blood is collected from the animal and antisera are prepared. Further fractionation of the antisera to enrich for antibodies reactive to the protein can be done if desired. See Harlow and Lane.

Monoclonal antibodies may be obtained by various techniques familiar to those skilled in the art. Briefly, spleen cells from an animal immunized with a desired antigen are immortalized, commonly by fusion with a myeloma cell. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 μM, typically at least about 100 μM, more typically at least about 30 μM, preferably at least about 10 μM, and more preferably at least about 3 μM or better; including 1 μM, 300 nM, 100 nM, 30 nM, etc.

The antibodies, including antigen binding fragments, of this invention can have significant diagnostic or therapeutic value. They can be potent antagonists that bind to the interleukin and inhibit binding to the receptor or inhibit the ability of IL-1δ or IL-1ε to elicit a biological response. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the interleukin without inhibiting receptor binding. As neutralizing antibodies, they can be useful in competitive binding assays. They will also be useful in detecting or quantifying IL-1δ. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Mammalian IL-1δ and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al. (1997) *Nature Genetics* 15:146–156. These references are incorporated herein by reference.

The antibodies of this invention can also be used for affinity chromatography in isolating the IL-1δ. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified protein will be released. The protein may be used to purify antibody.

The antibodies may also be used to screen expression libraries for particular expression products. Usually the antibodies used in such a procedure will be labeled with a moiety allowing easy detection of presence of antigen by antibody binding.

Antibodies raised against an IL-1δ or IL-L1ε will also be used to raise anti-idiotypic antibodies. These will be useful in detecting or diagnosing various immunological conditions related to expression of the protein or cells which express receptors for the protein. They also will be useful as agonists or antagonists of the interleukin, which may be competitive inhibitors or substitutes for naturally occurring ligands.

Binding Agent: IL-1δ or :IL-1ε Protein Complex

An IL-1δ or IL-1ε protein that specifically binds to or that is specifically immunoreactive with an antibody e.g., such as a polyclonal antibody, generated against a defined immunogen, e.g., such as an immunogen consisting of an amino acid sequence of SEQ ID NO: 2, 4, 6, 13, or 15 or fragments thereof or a polypeptide generated from the nucleic acid of SEQ ID NO: 1, 3, 5, 12, or 14, is typically determined in an immunoassay. Included within the metes and bounds of the present invention are those nucleic acid sequences described herein, including functional variants, that encode polypeptides that bind to polyclonal antibodies generated against the prototypical IL-1δ or IL-1ε proteins as structurally and functionally defined herein. The immunoassay typically uses a polyclonal antiserum which was raised, e.g., to a protein of SEQ ID NO: 2, 4, 6, 13, or 15. This antiserum is selected to have low crossreactivity against other IL-1 family members, preferably form the same species, and any such crossreactivity is removed by immunoabsorption prior to use in the immunoassay.

In order to produce antisera for use in an immunoassay, the protein of SEQ ID NO: 2, 4, 6, 13, or 15 is isolated as described herein. For example, recombinant protein may be produced in a mammalian cell line. An appropriate host, e.g., an inbred strain of mice such as Balb/c, is immunized with the protein of SEQ ID NO: 2, 4, 6, 13, or 15 using a standard adjuvant, such as Freund's adjuvant, and a standard mouse immunization protocol (see Harlow and Lane). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-1 family members, e.g., IL-11α, IL-1β, IL-1RA, and IL-1γ, using a competitive binding immunoassay such as the one described in Harlow and Lane, supra, at pages 570–573. Preferably at least two IL-1 family members are used in this determination in conjunction with either IL-1δ or IL-1ε. These IL-1 family members can be produced as recombinant proteins and isolated using standard molecular biology and protein chemistry techniques as described herein.

Immunoassays in the competitive binding format can be used for the crossreactivity determinations. For example, the protein of SEQ ID NO: 2, 4, 6, 13, or 15 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2, 4, 6, 13, or 15. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the IL-1 like protein of SEQ ID NO: 2, 4, 6, 13, or 15). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 that is required, then the second protein is said to specifically bind to an antibody generated to the immunogen.

It is understood that these IL-1δ or IL-1ε proteins are members of a family of homologous proteins that comprise at least 5 so far identified genes. For a particular gene product, such as the IL-1δ or IL-1ε protein, the term refers not only to the amino acid sequences disclosed herein, but also to other proteins that are allelic, non-allelic or species variants. It also understood that the term "IL-1δ" or "IL-1ε" includes non-natural mutations introduced by deliberate mutation using conventional recombinant technology such as single site mutation, or by excising short sections of DNA encoding the respective proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring IL-1 related protein, e.g., the IL-1δ or IL-1ε protein shown in SEQ ID NO: 2, 4, 6, 13, or 15. The biological properties of the altered proteins can be determined by expressing the protein in an appropriate cell line and measuring the appropriate effect upon lymphocytes. Particular protein modifications considered minor would include conservative substitution of amino acids with similar chemical properties, as described above for the IL-1 family as a whole. By aligning a protein optimally with the protein of SEQ ID NO: 2, 4, 6, 13, and 15 and by using the conventional immunoassays described herein to determine immunoidentity, one can determine the protein compositions of the invention.

VII. Kits and Quantitation

Both naturally occurring and recombinant forms of the IL-1 like molecules of this invention are particularly useful in kits and assay methods. For example, these methods would also be applied to screening for binding activity, e.g., receptors for these proteins. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767–773, which is incorporated herein by reference. The latter describes means for testing binding by a plurality of defined polymers synthesized on a solid substrate. The development of suitable assays to screen for a receptor or agonist/antagonist homologous proteins can be greatly facilitated by the availability of large amounts of purified, soluble IL-1δ or IL-1ε in an active state such as is provided by this invention.

Purified IL-1δ can be coated directly onto plates for use in the aforementioned receptor screening techniques. However, non-neutralizing antibodies to these proteins can be used as capture antibodies to immobilize the respective interleukin on the solid phase, useful, e.g., in diagnostic uses.

This invention also contemplates use of IL-1δ, fragments thereof, peptides, and their fusion products in a variety of diagnostic kits and methods for detecting the presence of the protein or its receptor. Alternatively, or additionally, antibodies against the molecules may be incorporated into the kits and methods. Typically the kit will have a compartment containing either a defined IL-1δ peptide or gene segment or a reagent which recognizes one or the other. Typically, recognition reagents, in the case of peptide, would be a receptor or antibody, or in the case of a gene segment, would usually be a hybridization probe.

A preferred kit for determining the concentration of, e.g., IL-1δ, a sample would typically comprise a labeled compound, e.g., receptor or antibody, having known binding affinity for IL-1δ, a source of IL-1δ (naturally occurring or recombinant) as a positive control, and a means for separating the bound from free labeled compound, e.g., a solid phase for immobilizing the IL-1δ in the test sample. Compartments containing reagents, and instructions, will normally be provided.

Antibodies, including antigen binding fragments, specific for mammalian IL-1δ or a peptide fragment, or receptor fragments are useful in diagnostic applications to detect the presence of elevated levels of IL-1δ and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to IL-1δ or to a particular fragment thereof. These assays have also been extensively discussed in the literature. See, e.g., Harlow and Lane (1988) *Antibodies: A Laboratory Manual*, CSH., and Coligan (Ed.) (1991) and periodic supplements, *Current Protocols In Immunology* Greene/Wiley, New York.

Anti-idiotypic antibodies may have similar use to serve as agonists or antagonists of IL-1δ. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

Any of the aforementioned constituents of the diagnostic assays may be used without modification or may be modified in a variety of ways. For example, labeling may be achieved by covalently or non-covalently joining a moiety which directly or indirectly provides a detectable signal. In any of these assays, a test compound, IL-1δ, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The IL-1δ can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-1δ. These sequences can be used as probes for detecting levels of the IL-1δ in patients suspected of having an immunological disorder. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

VIII. Therapeutic Utility

This invention provides reagents with significant therapeutic value. The IL-1δ or IL-1ε (naturally occurring or recombinant), fragments thereof, mutein agonists and antagonists, and antibodies, along with compounds identified as having binding affinity to the interleukin or its receptor or antibodies, should be useful in the treatment of conditions exhibiting abnormal expression of the interleukin. Such abnormality will typically be manifested by immunological disorders. Additionally, this invention should provide therapeutic value in various diseases or disorders associated with abnormal expression or abnormal triggering of response to the interleukin. The mouse IL-γ has been suggested to be involved in tumors, allergies, and infectious diseases, e.g., pulmonary tuberculosis, leprosy, fulminant hepatitis, and viral infections, such as HIV. The IL-1δ and/or IL-1ε or antagonist may have similar function.

In addition, the dendritic cell expression profile shows human IL-1γ primarily expressed in activated dendritic cells. Activated dendritic cells are also a major producer of IL-12, and it is thought that this dendritic cell produced IL-12 plays a major role in directing a Th1 type response. The combination of IL-1γ and IL-12 should be extremely potent in inducing IFN-γ, suggesting that IL-1δ or IL-1ε, or antagonists thereof, may have similar function. It is possible that the combination of pro-inflammatory cytokines under certain circumstances could lead to septic shock. An antagonist, mutein or antibody, could prove very useful in this situation. See Rich (ed.) *Clinical Immunology: Principles and Practice*, Mosby.

Additionally, IL-1δ or IL-1ε being homologous members of the IL-1 family (Table 4) likely play a role in modulating of local and systemic inflammatory processes (See, Durum, et al. (1986) *Ann. Rev. Immunol.* 3:253), through the enhancement of blood flow, induction of chemoattractants, and the enhancement and adherence of adhesion molecules resulting in the accumulation of inflammatory cells such as macrophages and neutrophils at the site of inflammation. Additionally, it is likely that IL-1δ or IL-1ε induce fibroblast growth and may play a role in contributing to the pathogenesis of chronic inflammation, as in rheumatoid arthritis or periodontal disease.

IL-1δ or IL-1ε are also likely to play a role in systemic inflammatory reactions, such as fever, hypoglycemia, the acute phase response of the liver, reduced plasma iron and zinc, and increased plasma copper. A systemic reaction such as septic shock involves vasodilation, due to IL-1, most likely in combination with other cytokines, including, e.g., TNF, IFN-γ, and leukemia inhibitory factor (LIF). The newly described IL-1δ or IL-1ε are also likely to be similarly involved.

In the following, directed to IL-1δ, similar substitution of IL-1ε may be appropriate. Recombinant IL-1δ, mutein agonists or antagonists, or IL-1δ antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Receptor screening using IL-1δ or fragments thereof can be performed to identify molecules having binding affinity to the interleukin. Subsequent biological assays can then be utilized to determine if a receptor can provide competitive binding, which can block intrinsic stimulating activity. Receptor fragments can be used as a blocker or antagonist in that it blocks the activity of IL-1δ. Likewise, a compound having intrinsic stimulating activity can activate the receptor and is thus an agonist in that it simulates the activity of IL-1δ. This invention further contemplates the therapeutic use of antibodies to IL-1δ as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, (current ed.), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the likely high affinity binding between an IL-1δ and its receptors, low dosages of these reagents would be initially expected to be effective. And the signaling pathway suggests extremely low amounts of ligand may have effect. Thus, dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

IL-1δ fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y.

Another therapeutic approach included within the invention involves direct administration of reagents or compositions by any conventional administration techniques (e.g., but not restricted to local injection, inhalation, or administered systemically), to the subject with an inflammatory disorder. The reagent, formulation or composition may also be targeted to specific cells or receptors by any of the methods described herein. The actual dosage of reagent, formulation or composition that modulates an inflammatory disorder depends on many factors, including the size and health of an organism, however one of one of ordinary skill in the art can use the following teachings describing the methods and techniques for determining clinical dosages. See, e.g., Spilker (1984) *Guide to Clinical Studies and Developing Protocols*, Raven Press, New York, particularly pages 7–13, 54–60; Spilker (1991) *Guide to Clinical Trials*, Raven Press, New York, especially pages 93–101; Craig and Stitzel (eds. 1986) *Modern Pharmacology* 2d ed., Little, Brown, Boston, especially pages 127–33; Speight (ed. 1987) *Avery's Drug Treatment: Principles and Practice of Clinical Pharmacology and Therapeutics*, 3d ed., Williams and Wilkins, Baltimore, pages 50–56; and Tallarida, et al. (1988) *Principles in General Pharmacology*, Springer-Verlag, New York, pages 18–20; which describe how to determine the appropriate dosage; but, generally, in the range of about between 0.5 ng/ml and 500 μg/ml inclusive final concentration are administered per day to an adult in a pharmaceutically-acceptable carrier. The therapy of this invention may be combined with or used in association with other therapeutic agents, particularly agonists or antagonists of other IL-1 family members.

T helper cells mediate effector functions in infectious, allergic, or autoimmune diseases through production of cytokines. CD4 positive T cells can be divided into Th1 and Th2 subsets on the basis of their cytokine profile upon antigen stimulation. We have recently obtained evidence that Th1 and Th2 cells differ in responsiveness and receptor expression for IL-1 family molecules. See, e.g., Robinson, et al. (1997) *Immunity* 7:571–581. Whereas Th1 cells respond to IL-1γ, Th2 cells respond to IL-1α. This differential responsiveness between Th1 and Th2 cells to IL-1γ and IL-1α, respectively, may have profound implications for regulation of ongoing Th cell responses. The novel IL-1 molecules described here could play a similar role in either supporting a Th1 or Th2 response, depending on the presence or absence of their cognate IL-1 receptors on the cell surface of these immune cells; e.g., IL-1RD4 (ST2) is an orphan IL-1-like receptor exclusively expressed on the Th2 subset. See, e.g., Lohning, et al. (1998) *Proc. Nat'l Acad. Sci. USA* 95:6930–6935; and U.S. Ser. No. 09/040,714, which are incorporated herein by reference. The expression profile of the novel IL-1 proteins here described (in particular IL-1ε) indicates that IL-1ε could be the ligand for IL-1RD4 and, as such, could be important for Th2 effector function.

IX. Receptors

The description of the IL-1δ ligand herein provides means to identify a receptor, as described above. Such receptor should bind specifically to the IL-1δ with reasonably high affinity. Various constructs are made available which allow either labeling of the IL-1δ to detect its receptor. For example, directly labeling IL-1δ, fusing onto it markers for secondary labeling, e.g., FLAG or other epitope tags, etc., will allow detection of receptor. This can be histological, as an affinity method for biochemical purification, or labeling or selection in an expression cloning approach. A two-hybrid selection system may also be applied making appropriate constructs with the available IL-1δ sequences. See, e.g., Fields and Song (1989) *Nature* 340:245–246. Typically, a cytokine will bind to its receptor at a Kd of at least about 30 μM, preferably at least about 10 μM, and more preferably at least about 3 μM or better; including 1 μM, 300 nM, 100 nM, 30 nM, etc.

Generally, descriptions of how to make IL-1δ will be analogously applicable to embodiments directed to IL-1ε reagents and compositions.

The broad scope of this invention is best understood with reference to the following examples, which are not intended to limit the inventions to the specific embodiments.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms an expression of excluding any equivalents of the features shown and described or portions thereof, but it is recognized that various modifications are possible with the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Meth. Enzymol.*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to IL-4 and IL-10 may be applied to IL-1δ and/or IL-1ε, as described, e.g., in U.S. Pat. No. 5,017,691 (IL-4), U.S. Ser. No. 07/453,951 (IL-10), and U.S. Ser. No. 08/110,683 (IL-10 receptor), each of which is incorporated herein by reference for all purposes.

II. Amplification of IL-1δ or IL-1ε fragment by PCR

There are various methods of isolating the DNA sequences encoding IL-1δ and IL-1ε proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding thymokine proteins, or probes can be designed for use in amplification techniques such as PCR, for the isolation of DNA encoding IL-1δ and IL-1ε proteins.

Various methods of amplifying target sequences, such as the polymerase chain reaction, can also be used to prepare DNA encoding IL-1δ and IL-1ε proteins. Polymerase chain reaction (PCR) technology is used to amplify such nucleic acid sequences directly from mRNA, from cDNA, and from genomic libraries or cDNA libraries. The isolated sequences encoding IL-1δ or IL-1ε proteins may also be used as templates for PCR amplification.

In PCR techniques, oligonucleotide primers complementary to two 5' regions in the DNA region to be amplified are synthesized. The polymerase chain reaction is then carried out using the two primers. See Innis et al. (current eds.) *PCR Protocols: A Guide to Methods and Applications* Academic Press, San Diego, Calif. Primers can be selected to amplify the entire regions encoding a full-length IL-1δ or IL-1ε proteins or to amplify smaller DNA segments as desired. Once such regions are PCR-amplified, they can be sequenced and oligonucleotide probes can be prepared from sequence obtained using standard techniques. These probes can then be used to isolate DNA's encoding IL-1δ or IL-1ε proteins.

Oligonucleotides for use as probes are chemically synthesized according to the solid phase phosphoramidite triester method first described by Beaucage and Carruthers (1983) *Tetrahedron Lett.* 22(20): 1859–1862, or using an automated synthesizer, as described in Needham-VanDevanter et al. (1984) *Nucleic Acids Res.* 12: 6159–6168. Purification of oligonucleotides is performed e.g., by native acrylamide gel electrophoresis or by anion-exchange HPLC as described in Pearson and Regnier (1983) *J. Chrom.* 255: 137–149. The sequence of the synthetic oligonucleotide can be verified using the chemical degradation method of Maxim and Gilbert in Grossman and Moldave (eds.) (1980) *Methods in Enzymology* 65: 499–560 Academic Press, New York.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

To identify a homologous IL-1δ or IL-1ε proteins, degenerate oligonucleotides are designed which corresponded to conserved regions among known IL-1 family members. The primers are used for polymerase chain reactions on mouse genomic DNA followed by subcloning the PCR products using restriction sites placed at the 5' ends of the primers, picking individual E. coli colonies carrying these subcloned inserts, and using a combination of random sequencing and hybridization analysis to eliminate known IL-1 family members.

Subsequently, PCR products are gel-purified, digested with appropriate restriction enzymes, gel-purified again, and subcloned in the Bluescript vector (Stratagene, San Diego, Calif.). Bacterial colonies carrying individual subclones are picked into 96 well microtiter plates, and multiple replicas are prepared by plating the cells onto nitrocellulose. The replicate filters are hybridized to probes representing known members of the IL-1 family, and DNA is prepared from non-hybridizing colonies for sequence analysis.

Two appropriate forward and reverse primers are selected using the sequences supplied herein (see Table 1 or 2) and common knowledge. See, e.g., Innis, et al. (current eds.) *PCR Protocols: A Guide to Methods and Applications* Academic Press, San Diego, Calif.; and Dieffenbach and Dveksler (current eds.) *PCR Primer: A Laboratory Manual* Cold Spring Harbor Press, CSH, NY. RT-PCR is used on an appropriate mRNA sample selected for the presence of message to produce a cDNA, e.g., a monocyte or macrophage cell sample. The original isolate of IL-1δ was from a whole mouse cDNA library, and for the IL-1ε from a mouse placenta.

Full length clones may be isolated by hybridization of cDNA libraries from appropriate tissues pre-selected by PCR signal.

As is commonly known, PCR primers are typically designed to contain at least 15 nucleotides, e.g., 15–30 nucleotides. The design of IL-1δ or IL-1ε specific primers containing 21 nucleotides, e.g., that code for IL-1δ or IL-1ε polypeptides containing at least 4 amino acids from the IL-1δ or IL-1ε domains are described as follows. Other PCR primers designed to amplify other IL-1δ or IL-1ε polypeptide fragments will be designed in a similar fashion, e.g., mutagenesis primers. Preferably, most or all of the nucleotides in such a primer encode conserved amino acids, e.g., amino residues of SEQ. ID NO: 2, 4, 6, 13, and 15, including IL-1δ or IL-1ε-specific amino acids as described herein. For example, primers containing at least 40% IL-1δ or IL-1ε-conserved amino acids can be used. Such a primer, containing 21 nucleotides, can include sequences encoding at least 3/7, 4/7, 5/7, 6/7 or 7/7 IL-1δ or IL-1ε-conserved amino acids. Once IL-1δ or IL-1ε amino acids are selected as templates against which primer sequences are to be designed, the primers can be synthesized using, e.g., standard chemical methods. Due to the degeneracy of the genetic code and the bias of preferred species variants, such primers should be designed to include appropriate degenerate sequences, as can be readily determined using common knowledge.

Based on the guidelines presented above, examples of IL-1δ or IL-1ε-conserved amino acid peptides that can be used as templates for the design of IL-1δ or IL-1ε specific primers are as follows. Additional examples can be found by analysis of sequence alignments of IL-1δ or IL-1ε polypeptides (Tables 1–3). Primers can be designed to amplify various structural features or domains, e.g., a 4–10 amino acid region of either IL-1δ or IL-1ε peptide that corresponds to any one of the 12 β strands could be amplified using this strategy. Depending on the length of the primer desired primers can be designed, e.g., to correspond to 4–7 consecutive amino acids of any of the segments shown below.

1. LeuCysPheArgMetLysAsp (corresponding to amino acid residues 8 to 14 of murine IL-1δ; see SEQ ID NO: 2).
2. ValLeuTyrLeuHisAsn (corresponding to amino acid residues 19 to 24 of murine IL-1δ; see SEQ ID NO: 2).
3. GlnLeuLeuAlaGly (corresponding to amino acid residues 26 to 30 of murine IL-1δ; see SEQ ID NO: 2).
4. IleSerValValProAsn (corresponding to amino acid residues 43 to 48 of murine IL-1δ; see SEQ ID NO: 2).
5. SerProValIleLeuGlyVal (corresponding to amino acid residues 56 to 62 of murine IL-1δ; see SEQ ID NO: 2).
6. GlnCysLeuSerCysGlyThr (corresponding to amino acid residues 67 to 73 of murine IL-1δ; see SEQ ID NO: 2).
7. ProIleLeuLysLeuGlu (corresponding to amino acid residues 77 to 82 of murine IL-1δ; see SEQ ID NO: 2).
8. PheTyrArgArgAspMetGly (corresponding to amino acid residues 101 to 107 of murine IL-1δ; see SEQ ID NO: 2).
9. LeuThrSerSerPheGluSer (corresponding to amino acid residues 108 to 114 of murine IL-1δ; see SEQ ID NO: 2).
10. PheLeuCysThrSer (corresponding to amino acid residues 121 to 125 of murine IL-1δ; see SEQ ID NO: 2).
11. GlnProValArgLeuThr (corresponding to amino acid residues 130 to 135 of murine IL-1δ; see SEQ ID NO: 2).
12. PheTyrPheGlnGln (corresponding to amino acid residues 150 to 154 of murine IL-1δ; see SEQ ID NO: 2).
13. ArgAlaLeuAspAlaSerLeu (corresponding to amino acid residues 49 to 55 of murine IL-1δ; see SEQ ID NO: 2).

For murine IL-1ε:
1. SerLeuArgHisValGlnAsp (corresponding to amino acid residues 13 to 19 of murine IL-1ε; see SEQ ID NO: 6).
2. ValTrpIleLeuGlnAsn (corresponding to amino acid residues 24 to 29 of murine IL-1ε; see SEQ ID NO: 6).
3. IleLeuThrAlaVal (corresponding to amino acid residues 31 to 35 of murine IL-1ε; see SEQ ID NO: 6).
4. IleThrLeuLeuProCys (corresponding to amino acid residues 46 to 51 of murine IL-1ε; see SEQ ID NO: 6).
5. AspProThrTyrMetGlyVal (corresponding to amino acid residues 63 to 69 of murine IL-1ε; see SEQ ID NO: 6).
6. SerCysLeuPheCysThrLys (corresponding to amino acid residues 74 to 80 of murine IL-1ε; see SEQ ID NO: 6).
7. ProValLeuGlnLeuGly (corresponding to amino acid residues 85 to 90 of murine IL-1ε; see SEQ ID NO: 6).
8. PheTyrHisLysLysSerGly (corresponding to amino acid residues 109 to 115 of murine IL-1ε; see SEQ ID NO: 6).
9. ThrThrSerThrPheGluSer (corresponding to amino acid residues 116 to 122 of murine IL-1ε; see SEQ ID NO: 6).
10. PheIleAlaValCys (corresponding to amino acid residues 129 to 133 of murine IL-1ε; see SEQ ID NO: 6).
11. CysProLeuIleLeuThr (corresponding to amino acid residues 138 to 143 of murine IL-1ε; see SEQ ID NO: 6).
12. PheGluMetIleVal (corresponding to amino acid residues 154 to 158 of murine IL-1ε; see SEQ ID NO: 6).

For primate IL-1ε:
1. IleThrGlyThrIleAsnAsp (corresponding to amino acid residues 23 to 29 of primate IL-1ε; see SEQ ID NO: 15).
2. ValTrpThrLeuGlnGly (corresponding to amino acid residues 34 to 39 of primate IL-1ε; see SEQ ID NO: 15).
3. AsnLeuValAlaVal (corresponding to amino acid residues 41 to 45 of primate IL-1ε; see SEQ ID NO: 15).

4. ValAlaValIleThrCys (corresponding to amino acid residues 56 to 61 of primate IL-1ε; see SEQ ID NO: 15).
5. AspProIleTyrLeuGlyIle (corresponding to amino acid residues 73 to 79 of primate IL-1ε; see SEQ ID NO: 15).
6. MetCysLeuTyrCysGluLys (corresponding to amino acid residues 84 to 90 of primate IL-1ε; see SEQ ID NO: 15).
7. ProThrLeuGlnLeuLys (corresponding to amino acid residues 95 to 100 of primate IL-1ε; see SEQ ID NO: 15).
8. PheTyrArgAlaLysThrGly (corresponding to amino acid residues 119 to 125 of primate IL-1ε; see SEQ ID NO: 15).
9. ThrSerThrLeuGluSer (corresponding to amino acid residues 127 to 132 of primate IL-1ε; see SEQ ID NO: 15).
10. PheIleAlaSerSer (corresponding to amino acid residues 139 to 143 of primate IL-1ε; see SEQ ID NO: 15).
11. GlnProIleIleLeuThr (corresponding to amino acid residues 147 to 152 of primate IL-1ε; see SEQ ID NO: 15).
12. PheGluLeuAsnIle (corresponding to amino acid residues 163 to 167 of primate IL-1ε; see SEQ ID NO: 15).

As is described above, IL-1ε or IL-1δ primers, e.g., primers based on IL-1ε or IL-1δ sequences shown above, or portions thereof, can be used in PCR reactions to generate IL-1ε or IL-1δ, probes which can be used in standard screening methods to identify nucleic acids encoding IL-1ε or IL-1δ family members (see e.g., Ausubel, et al., supra).

III. Tissue Distribution of IL-1δ or IL-1ε

Message for the gene encoding IL-1δ has been detected in a mouse cDNA library. Message for IL-1ε has been detected in placenta tissue.

Southern Analysis: DNA (5 µg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation could include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO− T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30–1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFNγ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+ CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL-4 5 days, resting (D108); DC from monocytes GM-CSF, IL-4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100).

Using the information described herein for cloning species variants, expression of human IL-1ε or IL-1δ can be determined as above using a human homologue as for a detectable probe.

Tissue distribution of transcripts derived from IL-1δ and IL-1ε were determined in experiments using an RNAse protection assay. Total RNA was prepared from adult brain, spleen, lung, liver and kidney by homogenization in guanidium thiocyantae and extraction with phenol, followed by centrifugation through 5.7 M cesium chloride (Sambrook, et al. (1987 and periodic updates) *Molecular Cloning: A laboratory Manual* Cold Spring Harbor Laboratory Press, Cold Spring Harbor, N.Y.). Ten micrograms of total RNA from each tissue, or ten micrograms of yeast tRNA, was used for RNAse protection assay. Riboprobes were synthesized using either T7 or T3 RNA polymerase on linerized templates that were cloned into pBluescript. Each mouse IL-1δ and IL-1ε probe contained 150–200 nucleotides from the antisense strand, linked to 25–50 nucleotides of vector sequence. Reagents were obtained from Ambion (Austin, Tex.) following standard manufacturer's protocols.

Tissue distribution of transcripts derived from IL-1δ and IL-1ε were compared with IL-1γ. The results demonstrate that IL-1ε expression is detectable in both embryonic, post-natal, and adult mice. An IL-1ε transcript (about 1.35 kD) is detectable at gestational day 7 and on postnatal day 1, adult IL-1δ transcripts (about 1.35 kD) were detectable in both the lung and kidney while not detected in brain, spleen and liver. For IL-1δ, an approximate 1.35 kD transcript was strongly detectable at gestational day 15 with a larger sized transcript (approximately 3.5 kD) less strongly detected. Similar results were observed at postnatal day 1. In adult tissue, a single sized IL-1δ transcript (approximately 1.8 kD) was detected in lung, liver, and kidney.

IV. Cloning of Species Counterparts of IL-1δ and IL-1ε

Various strategies are used to obtain species counterparts of mouse IL-1δ and IL-L1ε. One method is by cross hybridization using closely related species DNA probes. The degree of identity between mouse and human IL-1 counterparts typically is as high as 70%. It may be useful to go into evolutionarily similar species as intermediate steps. Another method is by using specific PCR primers based on the identification of blocks of similarity between human and mouse IL-1 counterparts, e.g., areas of highly conserved polypeptide sequence.

In addition, the IL-1α, IL-1β, and IL-1RA genes cluster on the same human chromosome. The fourth known member of the IL-1 family, IL-1γ, which is most closely related to IL-1β, has been mapped to a different human chromosome. Duplication of the intact IL-1α, IL-1β, IL-1RA gene cluster, a potential genetic event explaining a proliferation of additional family members, would suggest the existence of two as yet unidentified IL-1 genes at the location of the IL-1γ locus. IL-1δ and IL-1ε are potential candidates, and sequencing of the human IL-1γ locus may well lead to identification of the novel IL-1 genes.

V. Production of Mammalian IL-1δ Protein

An appropriate, e.g., GST, fusion construct is engineered for expression, e.g., in *E. coli*. For example, a mouse IGIF pGex plasmid is constructed and transformed into *E. coli*. Freshly transformed cells are grown in LB medium containing 50 μg/ml ampicillin and induced with IPTG (Sigma, St. Louis, Mo.). After overnight induction, the bacteria are harvested and the pellets containing IL-1δ are isolated. The pellets are homogenized in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the IL-1δ is filtered and passed over a glutathione-SEPHAROSE column equilibrated in 50 mM Tris-base pH 8.0. The fractions containing the IL-1δ-GST fusion protein are pooled and cleaved with thrombin (Enzyme Research Laboratories, Inc., South Bend, Ind.). The cleaved pool is then passed over a Q-SEPHAROSE column equilibrated in 50 mM Tris-base. Fractions containing IL-1δ are pooled and diluted in cold distilled $H_2O$, to lower the conductivity, and passed back over a fresh Q-SEPHAROSE column. Fractions containing IL-1δ are pooled, aliquoted, and stored in the −70° C. freezer.

Comparison of the CD spectrum with mouse IL-1β may suggest that the protein is correctly folded. See Hazuda, et al. (1969) *J. Biol. Chem.* 264:1689–1693.

Similar techniques will be applicable to a full length IL-1ε.

VI. Biological Assays with IL-1δ or IL-1ε

Biological assays confirmed IFN-γ inducing activity by IL-1γ on T cells. IL-1γ stimulates production of IFN-γ by purified NK cells, and that induction is strongly synergized with IL-12 or IL-2. Similar biological activity should be exhibited by IL-1δ and/or IL-1ε or their antagonists.

The family of interleukins 1 contains molecules, each of which is an important mediator of inflammatory disease. For a comprehensive review, see Dinarello (1996) "Biologic basis for interleukin-1 in disease" *Blood* 87:2095–2147. There are indications that the various IL-1's play important roles in the initiation of disease, including the recently identified IGIF/IL-1γ (e.g., Rothe, et al. (1997) "Active stage of autoimmune diabetes is associated with the expression of a novel cytokine, IGIF, which is located near Idd2." *J. Clin. Invest.* 99:469–474. The finding of novel proteins related to the IL-1 family furthers the identification of molecules that provide the molecular basis for initiation of disease and allow for the development of therapeutic strategies of increased range and efficacy.

Similar biological assays as applied to other known members of the family should be performed with purified IL-1δ or IL-1ε.

VII. Preparation of Antibodies Specific for IL-1δ or IL-1ε

Inbred Balb/c mice are immunized intraperitoneally with recombinant forms of the protein, e.g., purified soluble IL-1δ- or IL-1ε-FLAG or stable transfected NIH-3T3 cells. Animals are boosted at appropriate time points with protein, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response.

Monoclonal antibodies may be made. For example, splenocytes are fused with an appropriate fusion partner and hybridomas are selected in growth medium by standard procedures. Hybridoma supernatants are screened for the presence of antibodies which bind to the desired IL-1γ, e.g., by ELISA or other assay. Antibodies which specifically recognize IL-1δ or IL-1ε may also be selected or prepared.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156–4160; Barry, et al. (1994) *BioTechniques* 16:616–619; and Xiang, et al. (1995) *Immunity* 2: 129–135.

VIII. Production of Fusion Proteins with IL-1δ or IL-1ε

Various fusion constructs are made with IL-1δ or IL-1ε. This portion of the gene is fused to an epitope tag, e.g., a FLAG tag, or to a two hybrid system construct. See, e.g., Fields and Song (1989) *Nature* 340:245–246.

The epitope tag may be used in an expression cloning procedure with detection with anti-FLAG antibodies to detect a binding partner, e.g., receptor for the respective IL-1. The two hybrid system may also be used to isolate proteins which specifically bind to IL-1δ or IL-1ε.

IX. Mapping of IL-1δ or IL-1ε

Chromosome spreads were prepared. In situ hybridization was performed on chromosome preparations obtained from phytohemagglutinin-stimulated lymphocytes cultured for 72 h. 5-bromodeoxyuridine was added for the final seven hours of culture (60 μg/ml of medium), to ensure a posthybridization chromosomal banding of good quality.

An appropriate fragment, e.g., a PCR fragment, was amplified with the help of primers on total B cell cDNA template, and cloned into an appropriate vector. The vector was labeled by nick-translation with $^3$H. The radiolabeled probe was hybridized to metaphase spreads as described in Mattei, et al. (1985) *Hum. Genet.* 69:327–331.

After coating with nuclear track emulsion (KODAK NTB$_2$), slides were exposed, e.g., for 18 days at 4° C. To avoid any slipping of silver grains during the banding procedure, chromosome spreads were first stained with buffered Giemsa solution and metaphase photographed. R-banding was then performed by the fluorochrome-photolysis-Giemsa (FPG) method and metaphases re photographed before analysis.

The results show that both IL-1δ and IL-1ε map to the centromeric region of mouse chromosome 2, IL-1A, Il-1B and IL-1RN occupy a 450 Kb stretch of chromosome 2 (2q13) that is distal to IL-1δ and IL-1ε. For comparison, IGIF/IL-1γ is on mouse chromosome 9.

X. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

XI. Isolation of a Receptor for IL-1δ or IL-1ε

An IL-1δ can be used as a specific binding reagent to identify its binding partner, by taking advantage of its specificity of binding, much like an antibody would be used. A binding reagent is either labeled as described above, e.g., fluorescence or otherwise, or immobilized to a substrate for panning methods.

The binding composition is used to screen an expression library made from a cell line which expresses a binding partner, i.e., receptor. Standard staining techniques are used to detect or sort intracellular or surface expressed receptor, or surface expressing transformed cells are screened by panning. Screening of intracellular expression is performed by various staining or immunofluorescence procedures. See also McMahan, et al. (1991) *EMBO J.* 10:2821–2832.

For example, on day 0, precoat 2-chamber permanox slides with 1 ml per chamber of fibronectin, 10 ng/ml in PBS, for 30 min. at room temperature. Rinse once with PBS. Then plate COS cells at 2–3×10$^5$ cells per chamber in 1.5 ml of growth media. Incubate overnight at 37° C.

On day 1 for each sample, prepare 0.5 ml of a solution of 66 μg/ml DEAE-dextran, 66 μM chloroquine, and 4 μg DNA in serum free DME. For each set, a positive control is prepared, e.g., of IL-1γ-FLAG cDNA at 1 and ½00 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 μl/ml of 1 M NaN$_3$ for 20 min. Cells are then washed with HBSS/saponin 1×. Add appropriate IL-1δ or IL-1δ/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min., which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min. at 85–90° C.

Evaluate positive staining of pools and progressively subclone to isolation of single genes responsible for the binding.

Alternatively, IL-1δ reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a IL-1δ fusion construct, or by use of antibodies raised against the first antibodies. Recursive cycles of selection and amplification lead to enrichment of appropriate clones and eventual isolation of receptor expressing clones.

Phage expression libraries can be screened by mammalian IL-1δ. Appropriate label techniques, e.g., anti-FLAG antibodies, will allow specific labeling of appropriate clones.

All citations herein are incorporated herein by reference to the same extent as if each individual publication or patent application was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A binding composition comprising an antigen binding site from an antibody, which specifically binds to a mature polypeptide comprising at least 8 contiguous amino acid residues from SEQ ID NO: 2.

2. The binding compound of claim 1, wherein said binding compound is an Fv, Fab, or Fab2 fragment.

3. A kit comprising said binding compound of claim 1, and:
   a) a compartment comprising said binding compound; and/or
   b) instructions for use or disposal of reagents in said kit.

4. A composition comprising:
   a) a sterile binding compound of claim 1, or
   b) said binding compound of claim 1 and a carrier, wherein said carrier is:
      i) an aqueous compound, including water, saline, and/or buffer; and/or
      ii) formulated for oral, rectal, nasal, topical, or parenteral administration.

5. A method of:
   A) making an antiserum comprising an antibody of claim 1, comprising immunizing a mammal with an immunogenic amount of a peptide comprising a 12 consecutive amino acid segment of SEQ ID NO: 2; thereby causing said antiserum to be produced; or
   B) producing an antigen:antibody complex, comprising contacting a rodent IL-1δ protein with a binding compound of claim 1; thereby allowing said complex to form.

6. The binding compound of claim 1, wherein said antibody is a polyclonal antibody.

7. The binding compound of claim 1, wherein said antibody is detectably labeled.

8. The binding compound of claim 1, wherein said at least 8 contiguous amino acid residues of SEQ ID NO: 2 is selected from the group consisting of residues 8–24; 27–48; 56–73; 77–106; 108–125; 130–156; and 74–98.

9. The binding compound of claim 1, wherein said polypeptide comprising at least 12 contiguous amino acid residues from SEQ ID NO: 2.

10. The binding compound of claim 9, wherein said 12 contiguous amino acid segment is selected from:
   a) residues 9–25 of SEQ ID NO: 2;
   b) residues 43–63 of SEQ ID NO: 2;
   c) residues 56–68 of SEQ ID NO: 2;
   d) residues 77–89 of SEQ ID NO: 2;
   e) residues 109–121 of SEQ ID NO: 2;
   f) residues 121–132 of SEQ ID NO: 2;
   g) residues 135–147 of SEQ ID NO: 2.

* * * * *